US011589875B1

(12) United States Patent
Docherty et al.

(10) Patent No.: US 11,589,875 B1
(45) Date of Patent: Feb. 28, 2023

(54) ENDOSCOPIC CLIP APPARATUS AND METHODS

(71) Applicant: Gastrologic, LLC, San Diego, CA (US)

(72) Inventors: Michael Docherty, San Diego, CA (US); Roy Sullivan, Uxbridge, MA (US)

(73) Assignee: GastroLogic LLC, San Diego, CA (US)

( * ) Notice: Subject to any disclaimer, the term of this patent is extended or adjusted under 35 U.S.C. 154(b) by 0 days.

(21) Appl. No.: 17/895,727

(22) Filed: Aug. 25, 2022

Related U.S. Application Data

(60) Provisional application No. 63/260,569, filed on Aug. 25, 2021.

(51) Int. Cl.
*A61B 17/128* (2006.01)

(52) U.S. Cl.
CPC ................ *A61B 17/1285* (2013.01)

(58) Field of Classification Search
CPC ....... A61B 17/08; A61B 17/083; A61B 17/12; A61B 17/122; A61B 17/1227; A61B 17/128; A61B 17/1285; A61B 2017/12004; A61B 2017/2931
See application file for complete search history.

(56) References Cited

U.S. PATENT DOCUMENTS

| 3,958,576 A | 5/1976 | Komiya | |
| 5,520,701 A * | 5/1996 | Lerch | A61B 17/1285 606/151 |
| 6,165,183 A * | 12/2000 | Kuehn | A61B 17/064 606/151 |
| 6,991,634 B2 | 1/2006 | Sugiyama et al. | |
| 7,094,245 B2 | 8/2006 | Adams et al. | |

(Continued)

FOREIGN PATENT DOCUMENTS

| JP | 4921173 | 4/2012 |
| JP | 6518730 | 5/2019 |
| WO | WO2020/198259 A1 | 10/2020 |

OTHER PUBLICATIONS

Daram et al., Benchtop testing and comparisons among three types of through-the-scope endoscopic clipping devices, Surgical Endoscopy (journal), Jan. 5, 2013, pp. 1521-1529, 27-5, Springer Science+Business Media, New fork City USA.

(Continued)

*Primary Examiner* — Ryan J. Severson
(74) *Attorney, Agent, or Firm* — Waller Lansden Dortch & Davis, LLP; Matthew C. Cox

(57) ABSTRACT

An endoscopic clip apparatus includes a clip sleeve defining an interior passage along a longitudinal axis and having a distal end with a plurality of openings defined in the distal end. A clip including a plurality of arms is disposed in the clip sleeve, and each arm includes a distal tip extending from the clip sleeve through one of the plurality of openings. Each arm includes a convex curved section oriented away from the longitudinal axis. The clip sleeve and clip are axially moveable relative to each other such that when the clip sleeve travels over the convex curved section of each arm toward the distal tip of each arm, each arm is constrained by the clip sleeve and each distal tip advances toward the longitudinal axis to grasp tissue.

29 Claims, 33 Drawing Sheets

(56) References Cited

U.S. PATENT DOCUMENTS

| | | | |
|---|---|---|---|
| 7,122,041 B2 | 10/2006 | Surti | |
| 7,261,725 B2 * | 8/2007 | Binmoeller | A61B 17/083 |
| | | | 606/205 |
| 7,357,805 B2 * | 4/2008 | Masuda | A61B 17/122 |
| | | | 606/151 |
| 7,452,327 B2 | 11/2008 | Durgin et al. | |
| 7,494,461 B2 | 2/2009 | Wells et al. | |
| 7,727,247 B2 * | 6/2010 | Kimura | A61B 17/1285 |
| | | | 606/142 |
| 7,833,238 B2 | 11/2010 | Nakao | |
| 7,879,052 B2 | 2/2011 | Adams et al. | |
| 8,083,668 B2 | 12/2011 | Durgin et al. | |
| 8,088,061 B2 | 1/2012 | Wells et al. | |
| 8,444,660 B2 | 5/2013 | Adams et al. | |
| 8,491,610 B2 | 7/2013 | Karpiel et al. | |
| 8,551,119 B2 * | 10/2013 | Kogiso | A61B 17/1227 |
| | | | 606/143 |
| 8,663,247 B2 * | 3/2014 | Menn | A61B 17/00234 |
| | | | 606/142 |
| 8,685,048 B2 | 4/2014 | Adams et al. | |
| 8,690,899 B2 * | 4/2014 | Kogiso | A61B 17/1285 |
| | | | 606/151 |
| 8,709,027 B2 | 4/2014 | Adams et al. | |
| 8,764,774 B2 | 7/2014 | Sigmon, Jr. | |
| 8,915,837 B2 | 12/2014 | Wells et al. | |
| 8,939,997 B2 | 1/2015 | Martinez et al. | |
| 8,945,153 B2 * | 2/2015 | Surti | A61B 17/122 |
| | | | 606/142 |
| 8,974,371 B2 | 3/2015 | Durgin et al. | |
| 8,986,326 B2 | 3/2015 | Satake et al. | |
| 9,060,779 B2 | 6/2015 | Martinez | |
| 9,241,710 B2 | 1/2016 | Paz et al. | |
| 9,271,731 B2 | 3/2016 | Adams et al. | |
| 9,332,988 B2 | 5/2016 | Adams et al. | |
| 9,370,371 B2 | 6/2016 | Durgin et al. | |
| 9,445,821 B2 | 9/2016 | Wells et al. | |
| 9,474,585 B2 | 10/2016 | Pernot et al. | |
| 9,980,725 B2 | 5/2018 | Durgin et al. | |
| 10,143,479 B2 | 12/2018 | Adams et al. | |
| 10,172,623 B2 | 1/2019 | Adams et al. | |
| 10,172,624 B2 | 1/2019 | Adams et al. | |
| 10,307,169 B2 | 6/2019 | Wells et al. | |
| 10,610,237 B2 | 4/2020 | Estevez et al. | |
| 10,813,650 B2 | 10/2020 | Surti et al. | |
| 10,952,725 B2 | 3/2021 | Durgin et al. | |
| 10,952,743 B2 | 3/2021 | Adams et al. | |
| 2002/0177861 A1 | 11/2002 | Sugiyama et al. | |
| 2003/0069592 A1 * | 4/2003 | Adams | A61B 17/1285 |
| | | | 606/142 |
| 2004/0092978 A1 * | 5/2004 | Surti | A61B 17/122 |
| | | | 606/157 |
| 2005/0049618 A1 * | 3/2005 | Masuda | A61B 17/1285 |
| | | | 606/151 |
| 2005/0143767 A1 * | 6/2005 | Kimura | A61B 50/30 |
| | | | 606/158 |
| 2006/0155310 A1 * | 7/2006 | Binmoeller | A61B 17/122 |
| | | | 606/151 |
| 2006/0190013 A1 * | 8/2006 | Menn | A61B 17/128 |
| | | | 606/142 |
| 2006/0224165 A1 | 10/2006 | Surti et al. | |
| 2007/0282353 A1 * | 12/2007 | Surti | A61B 50/13 |
| | | | 606/142 |
| 2007/0282355 A1 * | 12/2007 | Brown | A61B 17/122 |
| | | | 606/151 |
| 2008/0140089 A1 * | 6/2008 | Kogiso | A61B 17/1285 |
| | | | 606/142 |
| 2008/0306491 A1 | 12/2008 | Cohen et al. | |
| 2009/0182352 A1 * | 7/2009 | Paz | A61B 17/08 |
| | | | 606/151 |
| 2009/0275957 A1 | 11/2009 | Harris et al. | |
| 2010/0016873 A1 | 1/2010 | Gayzik | |
| 2010/0152753 A1 * | 6/2010 | Menn | A61B 17/00234 |
| | | | 606/158 |
| 2010/0160935 A1 * | 6/2010 | Karpiel | A61B 17/10 |
| | | | 606/151 |
| 2011/0196390 A1 * | 8/2011 | Kogiso | A61B 17/1285 |
| | | | 606/151 |
| 2012/0041455 A1 * | 2/2012 | Martinez | A61B 17/1285 |
| | | | 606/142 |
| 2012/0109160 A1 * | 5/2012 | Martinez | A61B 17/08 |
| | | | 606/142 |
| 2012/0116419 A1 | 5/2012 | Sigmon, Jr. | |
| 2013/0226199 A1 | 8/2013 | Harris et al. | |
| 2015/0127021 A1 | 5/2015 | Harris et al. | |
| 2016/0174980 A1 | 6/2016 | Heftman | |
| 2018/0116677 A1 | 5/2018 | Estevez et al. | |
| 2018/0193021 A1 | 7/2018 | Martinez et al. | |
| 2018/0333156 A1 | 11/2018 | Hayashi et al. | |
| 2019/0059905 A1 * | 2/2019 | Adams | A61B 17/122 |
| 2019/0090883 A1 | 3/2019 | Adams et al. | |
| 2020/0138444 A1 | 5/2020 | Martinez et al. | |
| 2020/0205836 A1 | 7/2020 | Uesaka et al. | |
| 2021/0022746 A1 | 1/2021 | Smith et al. | |
| 2021/0137507 A1 | 5/2021 | Keren et al. | |
| 2021/0236134 A1 | 8/2021 | Tsuji | |
| 2021/0251633 A1 | 8/2021 | Uesaka et al. | |
| 2021/0267602 A1 | 9/2021 | Tsuji et al. | |
| 2021/0290240 A1 | 9/2021 | Yoshii | |
| 2021/0290244 A1 | 9/2021 | Fujimoto et al. | |
| 2021/0290245 A1 | 9/2021 | Yoshii et al. | |
| 2021/0298761 A1 | 9/2021 | Uesaka et al. | |
| 2021/0353296 A1 | 11/2021 | Fujimoto et al. | |

OTHER PUBLICATIONS

Olympus Corporation, Polygrab Tripod (FG-600U), Website, As early as Aug. 2017, https://medical.olympusamerica.com/products/forceps/polygrab-tripod-fg-600u.

PCT International Search Report, PCT/US2022/041555, dated Dec. 12, 2022.

PCT Written Opinion of the International Searching Authority, PCT/US2022/041555, dated Dec. 12, 2022.

\* cited by examiner

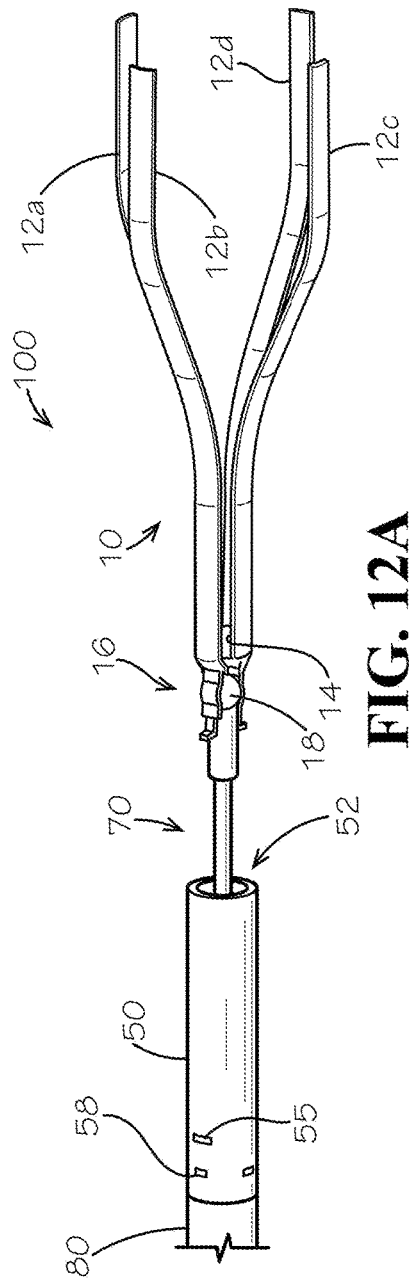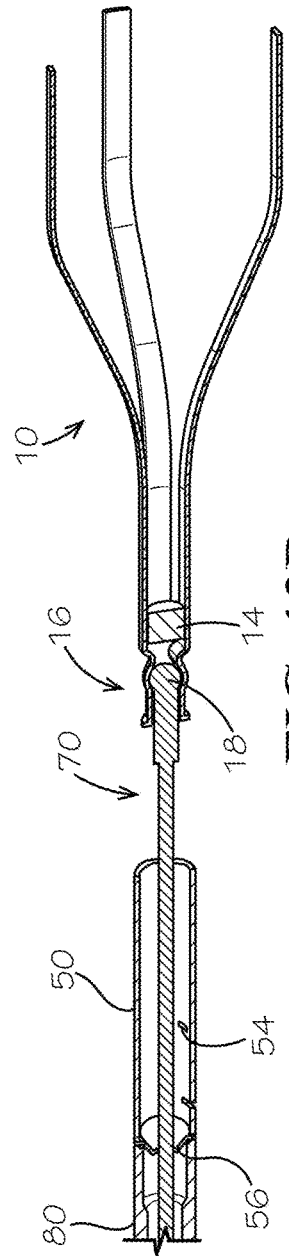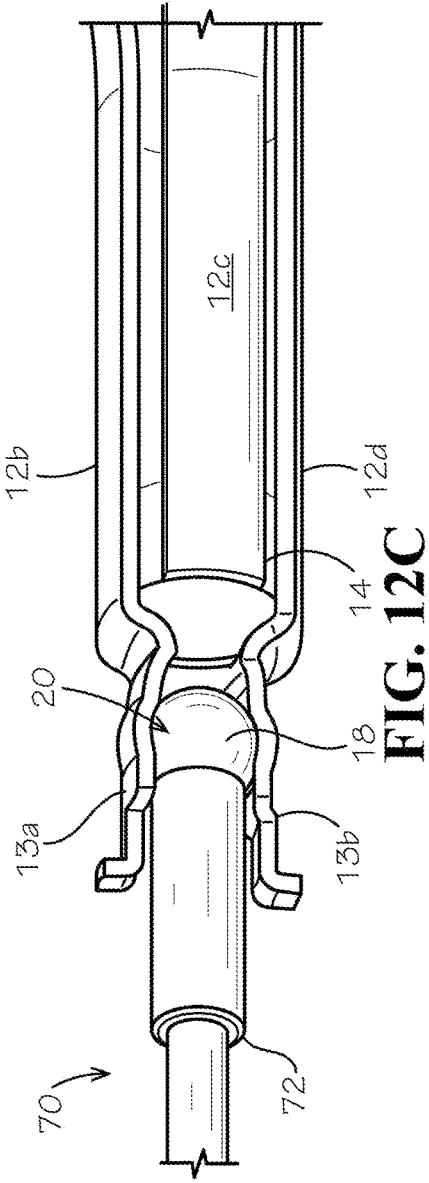

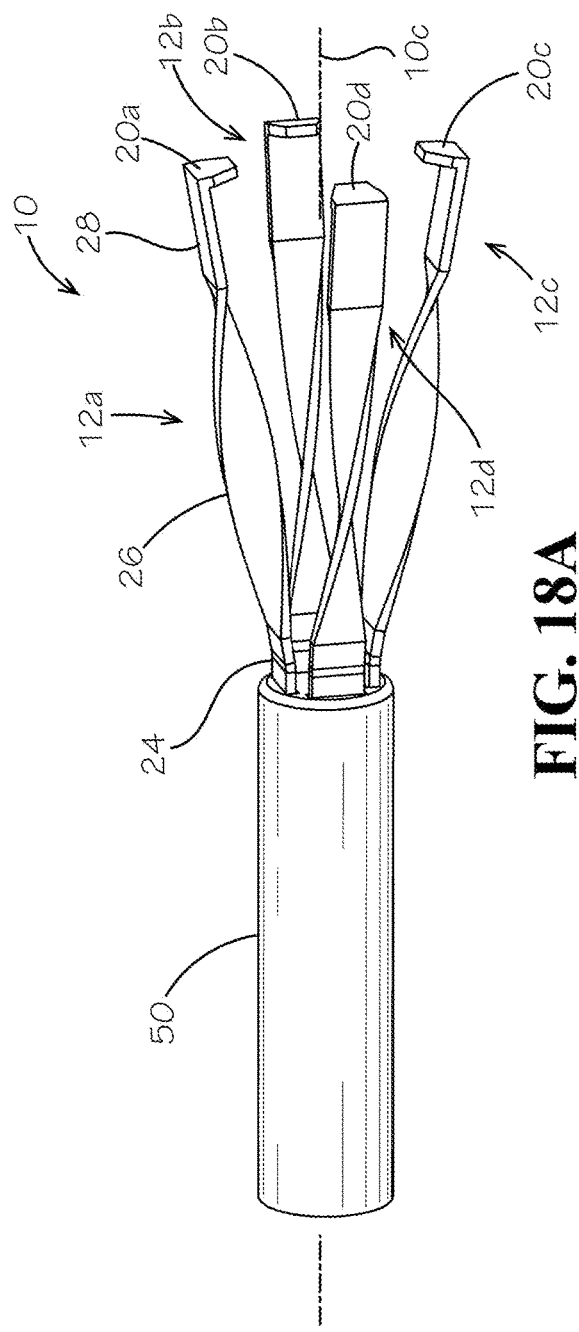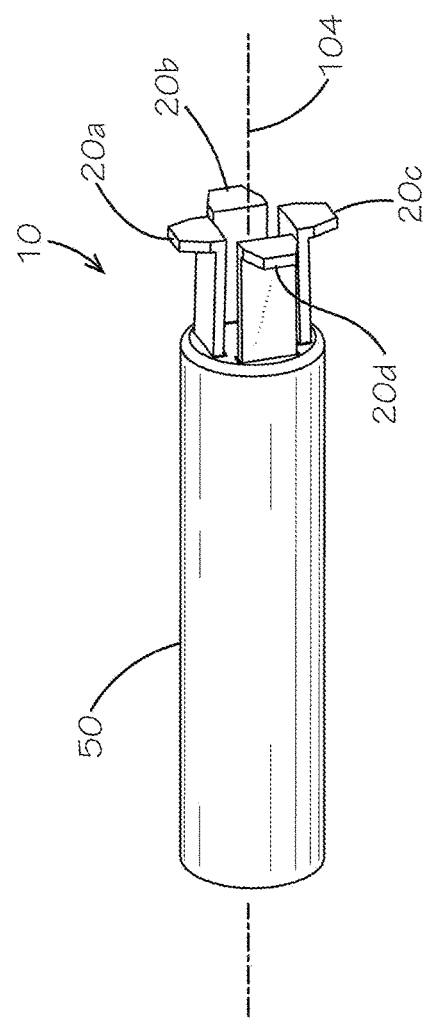
FIG. 18A
FIG. 18B

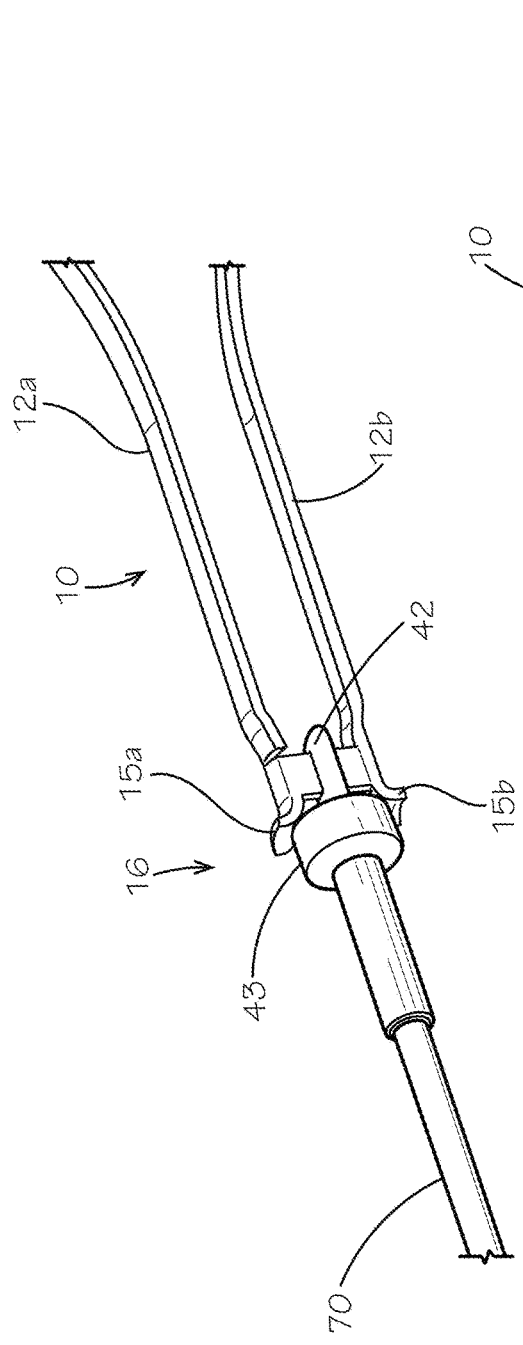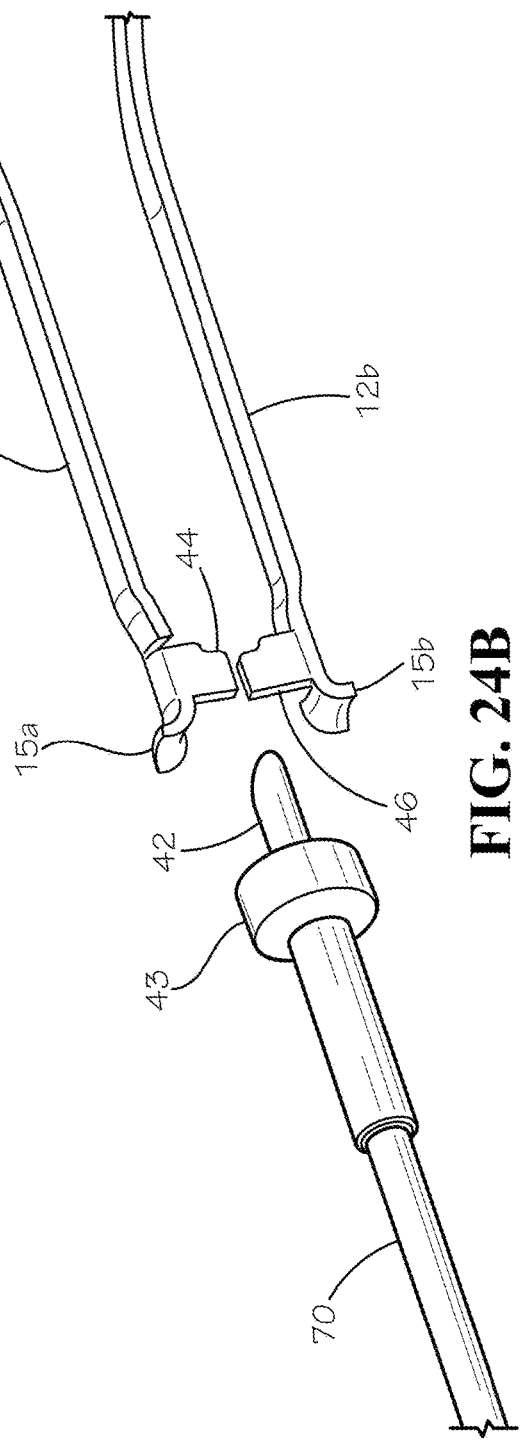

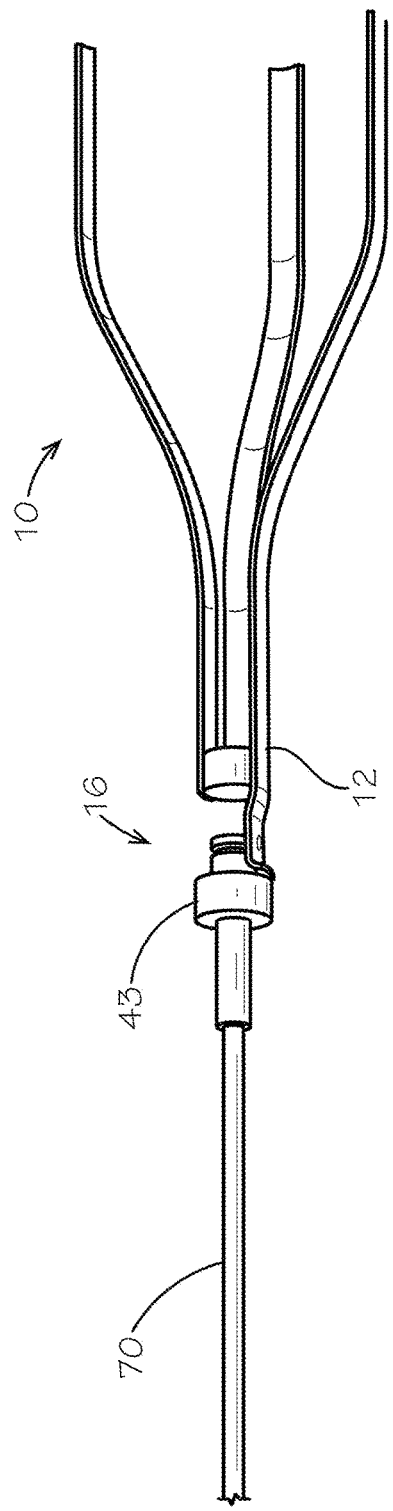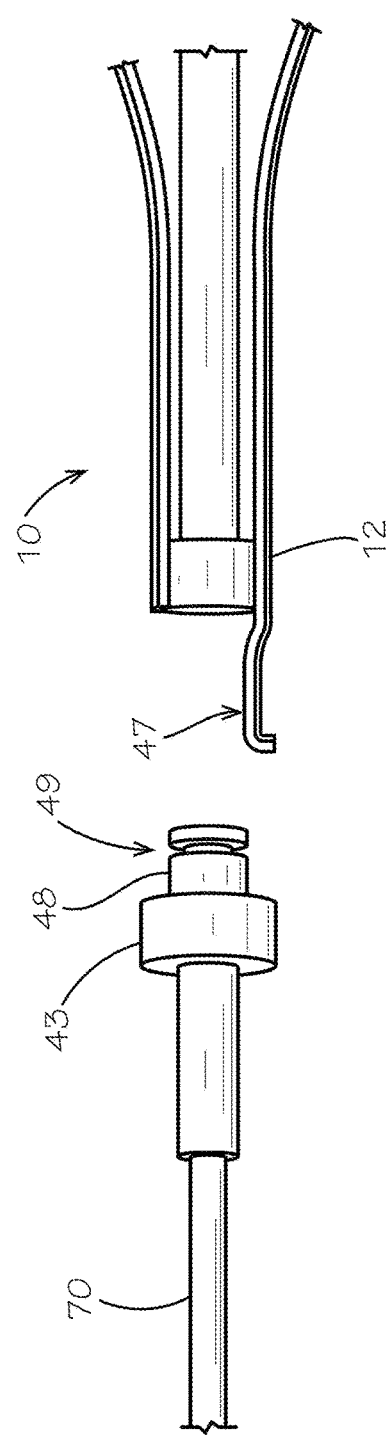
FIG. 26A
FIG. 26B

ENDOSCOPIC CLIP APPARATUS AND METHODS

CROSS-REFERENCE TO RELATED APPLICATION

The present non-provisional patent application claims priority to and benefit of U.S. Provisional Patent Application No. 63/260,569 filed Aug. 25, 2021 entitled Systems and Apparatuses for an Endoscopic Clip, all of which is hereby incorporated by reference in its entirety.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

TECHNICAL FIELD

The present disclosure generally relates to medical clips, and more particularly to endoscopic clip apparatuses and methods.

BACKGROUND

Conventional endoscopic clips include two or more arms that are pushed into tissues as the arms are swept through an arc motion until the arms come together. Conventional endoscopic clip arms are either made of thin metal that is stamped into the desired form or are machined from a monolithic piece of metal stock. These conventional arms experience tangential loading that causes them to buckle under loads created while capturing tissue. Because of this tendency to buckle, the arm size and shape is limited. While increasing the size of the arms may increase the arms' strength, the arms must still be able to pass through the lumen of an endoscope, which may be as small as 2.8 millimeters.

Conventional endoscopic clips may also fail to properly secure tissue or inadvertently loosen over time. Additionally, conventional endoscopic clips do not offer a sufficient mechanical advantage or precision control to perform certain types of operations.

What is needed then are improved endoscopic clip devices and associated methods.

BRIEF SUMMARY

This Brief Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

One aspect of the disclosure includes an apparatus. The apparatus may include a handle. The apparatus may include an endoscopic clip. The endoscopic clip may be coupled to the handle. The endoscopic clip may include a mounting hub. The mounting hub may include one or more slots. The endoscopic clip may include one or more arms. Each arm may extend from a slot of the one or more slots of the mounting hub. Each arm may include a helical shape. In response to a user of the apparatus pulling on a portion of the handle, the one or more arms may retract into the mounting hub, and the one or more arms may be drawn together at a center axis of the endoscopic clip.

Another aspect provides a detachable endoscopic clip apparatus including clip sleeve defining an interior passage along a longitudinal axis, the clip sleeve having a distal end with a plurality of openings defined in the distal end. A clip including a plurality of arms is disposed in the clip sleeve, each arm including a distal tip extending from the clip sleeve through one of the plurality of openings. Each arm includes a convex curved section oriented away from the longitudinal axis, wherein the clip sleeve and clip are moved axially relative to each other the clip sleeve travels over the convex curved section of each arm toward the distal tip of each arm, thereby constraining each arm and advancing each arm toward the longitudinal axis.

Another aspect provides an endoscopic clip apparatus including a clip sleeve defining an interior passage along a longitudinal axis and a distal end defining first, second, third and fourth openings. A clip is disposed in the clip sleeve, the clip including a first arm extending through the first opening, a second arm extending through the second opening, a third arm extending through the third opening, and a fourth arm extending through the fourth opening. Each of the first, second, third and fourth arms includes a section curving away from the longitudinal axis, and the clip sleeve and the clip are axially moveable relative to each other along the longitudinal axis.

Another aspect provides a method including (a) providing an endoscopic clip apparatus including a clip sleeve defining an interior passage along a longitudinal axis, the clip sleeve including distal end defining first, second, third and fourth openings, and including a clip disposed in the clip sleeve, the clip including a first arm extending through the first opening, a second arm extending through the second opening, a third arm extending through the third opening, and a fourth arm extending through the fourth opening, wherein each of the first, second, third and fourth arms includes a section curving away from the longitudinal axis; (b) translating the clip relative to the clip sleeve; and (c) constraining the arms in the clip sleeve such that the arms move toward the longitudinal axis.

Numerous other objects, advantages, and features of the present disclosure will be readily apparent to those of skill in the art upon a review of the following drawings and description of various embodiments.

BRIEF DESCRIPTION OF THE DRAWINGS

FIG. 12A is a partially exploded perspective view of an embodiment of an endoscopic clip apparatus.

FIG. 12B is a partially exploded cross-sectional perspective view of an embodiment of an endoscopic clip apparatus.

FIG. 12C is a detail partially exploded perspective view of an embodiment of an endoscopic clip apparatus including a release joint.

FIG. 18A is a perspective view of an embodiment of an endoscopic clip apparatus in a partially retracted position.

FIG. 18B is a perspective view of an embodiment of an endoscopic clip apparatus in a retracted position.

FIG. 24A is a perspective view of an endoscopic clip apparatus including a control wire and a clip with a release joint.

FIG. 24B is a perspective view of an endoscopic clip apparatus including a control wire and a clip with a release joint.

FIG. 26A is a perspective view of an endoscopic clip apparatus including a control wire and a clip with a release joint.

FIG. 26B is a perspective view of an endoscopic clip apparatus including a control wire and a clip with a release joint.

DETAILED DESCRIPTION

Figure 1:
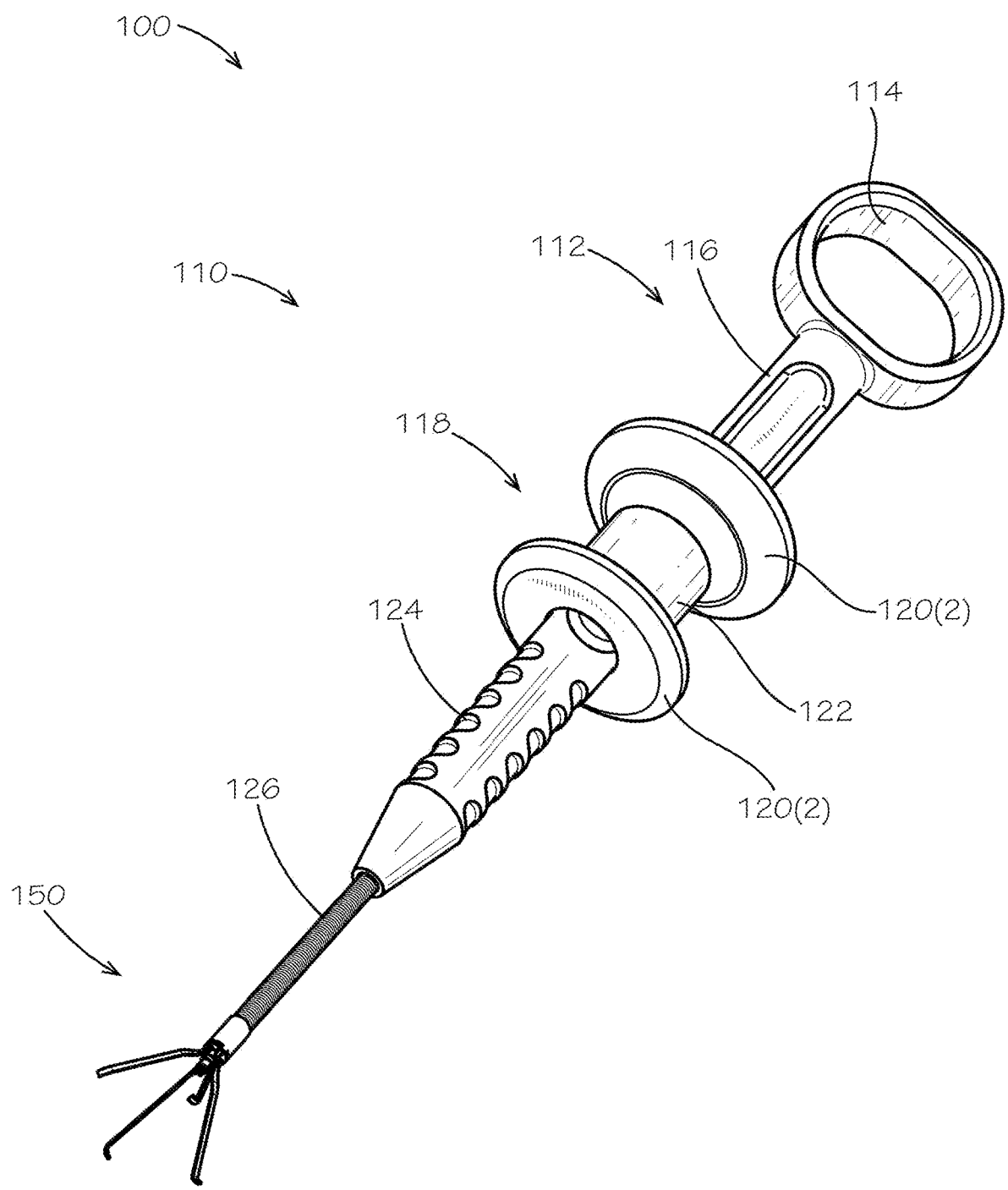
FIG. 1 is a perspective view illustrating one embodiment of an apparatus for an endoscopic clip.

While the making and using of various embodiments of the present disclosure are discussed in detail below, it should be appreciated that the present disclosure provides many applicable inventive concepts that are embodied in a wide variety of specific contexts. The specific embodiments discussed herein are merely illustrative of specific ways to make and use the disclosure and do not delimit the scope of the disclosure. Those of ordinary skill in the art will recognize numerous equivalents to the specific apparatus and methods described herein. Such equivalents are considered to be within the scope of this disclosure and are covered by the claims.

In the drawings, not all reference numbers are included in each drawing, for the sake of clarity. In addition, positional terms such as "upper," "lower," "side," "top," "bottom," etc. refer to the apparatus when in the orientation shown in the drawing. A person of skill in the art will recognize that the apparatus can assume different orientations when in use.

FIG. 1 depicts one embodiment of an apparatus 100. The apparatus 100 may include an apparatus for an endoscopic clip. The apparatus 100 may include a handle 110. The apparatus 100 may include an endoscopic clip 150.

The handle 110 may include a thumb pull 112. The thumb pull 112 may include a loop 114 wherein a user of the apparatus 100 may insert a finger or thumb. The thumb pull 112 may include a shaft 116. The handle 110 may include a finger pull 118. The finger pull 118 may be disposed around the shaft 116. The finger pull 118 may include a first and second stop 120(1)-(2). The finger pull 118 may include a stem 122 disposed around the shaft 116. The finger pull 118 may provide an area where the user of the apparatus 100 may grasp the handle 110. The user may grasp the thumb pull 112 with one hand and the finger pull 118 with the other hand in order to operate the apparatus 100. Some portions of the shaft 116 may include a ribbed structure 124. The handle 110 may include a tube 126. The tube 126 may couple the handle 110 to the endoscopic clip 150.

Figure 2:
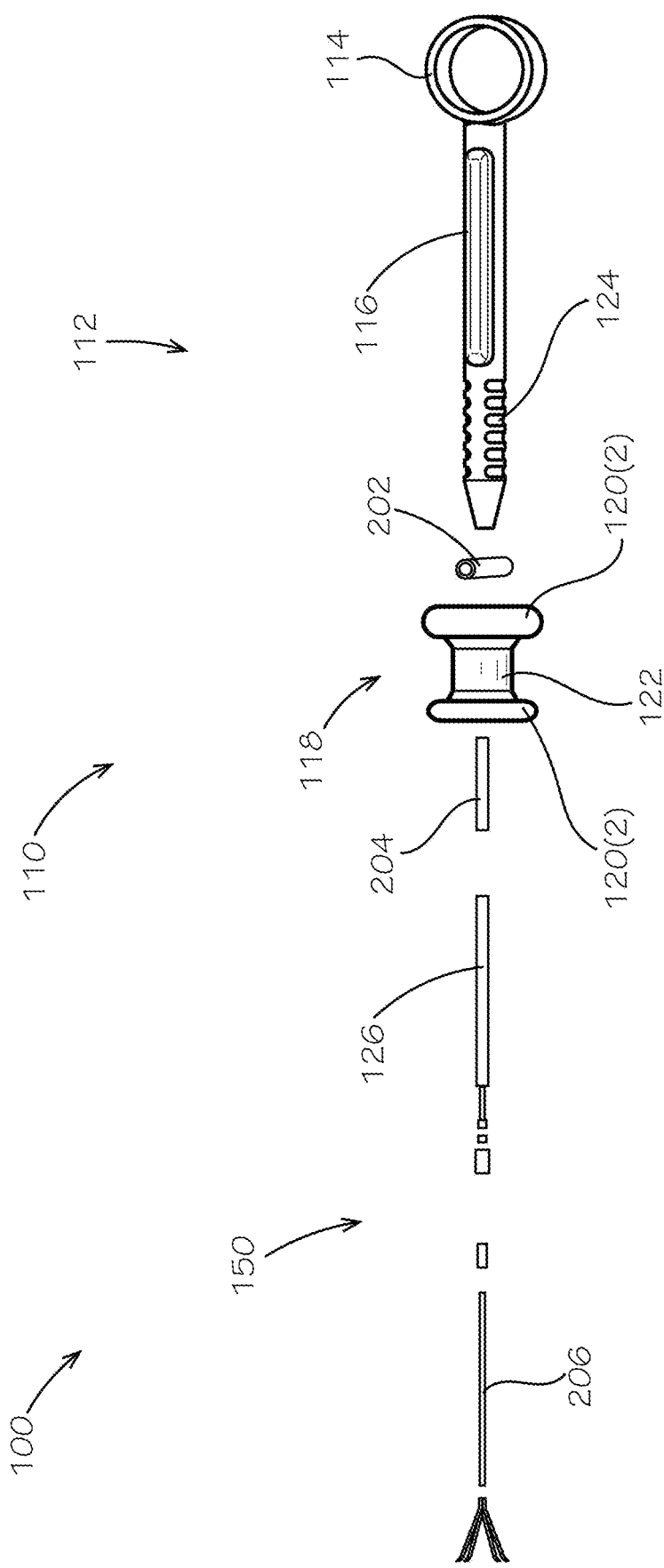
FIG. 2 is an exploded view illustrating another embodiment of the apparatus for the endoscopic clip of FIG. 1.

FIG. 2 depicts one embodiment of the apparatus 100. The apparatus 100 of FIG. 2 may include one or more components of the apparatus 100 of FIG. 1 such as the handle 110, the thumb pull 112, the loop 114, the shaft 116, the finger pull 118, the first and second stops 120(1)-(2), the stem 122, the ribbed structure 124, or the tube 126. The handle 110 may further include a spring clamp 202, a spring 204, and an actuation wire 206, which will be explained further below in relation to FIG. 9 and FIG. 10.

Figure 3:
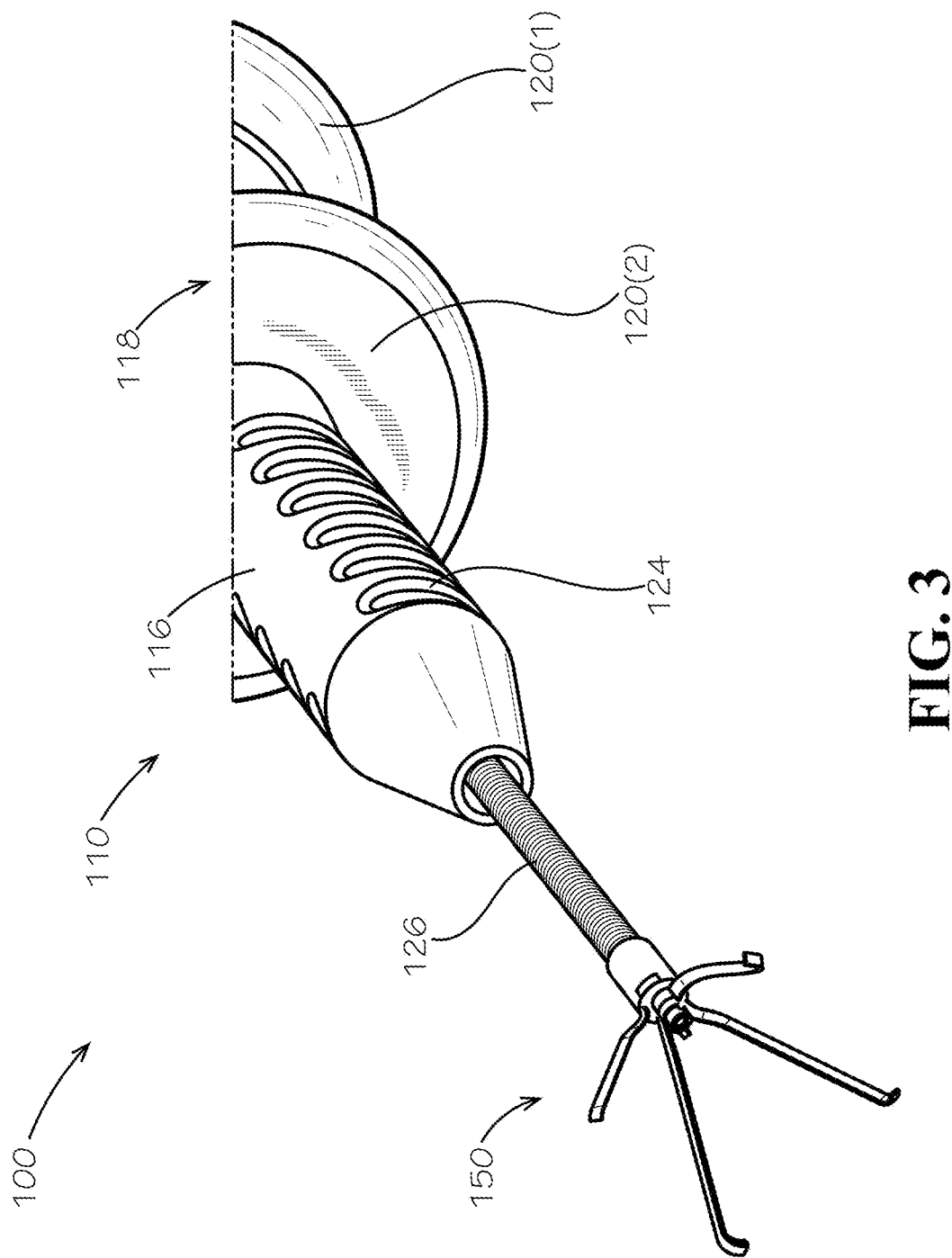
FIG. 3 is a perspective view illustrating another embodiment of the apparatus for the endoscopic clip of FIG. 1 emphasizing a distal end of the apparatus.

FIG. 3 depicts one embodiment of the apparatus 100. FIG. 3 depicts a closer-up view of the distal end of the apparatus 100. The distal end of the apparatus 100 may include the endoscopic clip 150.

Figure 4A:
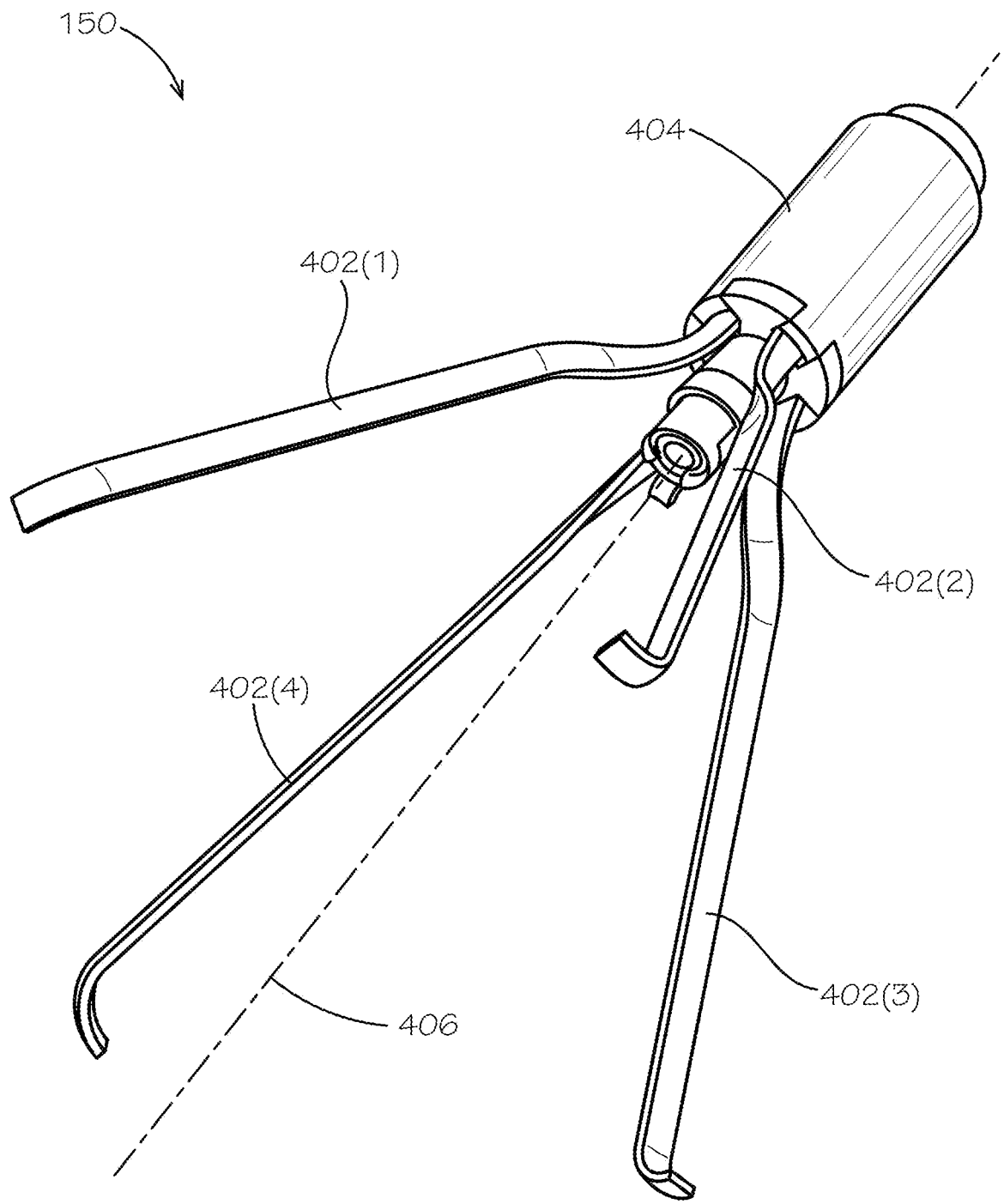
FIG. 4A is a perspective view illustrating one embodiment of an endoscopic clip.
Figure 4B:
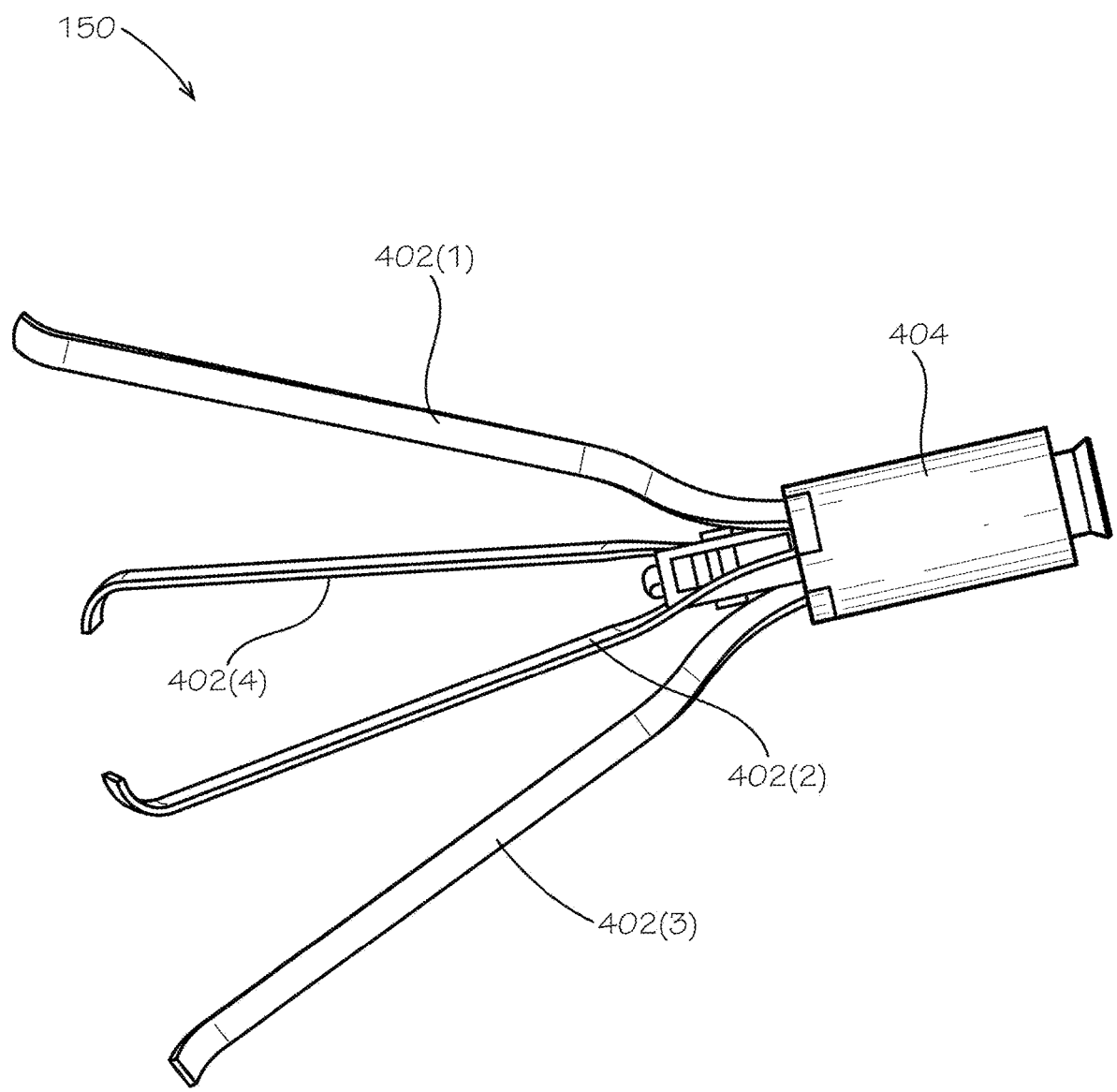
FIG. 4B is a side view illustrating one embodiment of an endoscopic clip.
Figure 4C:
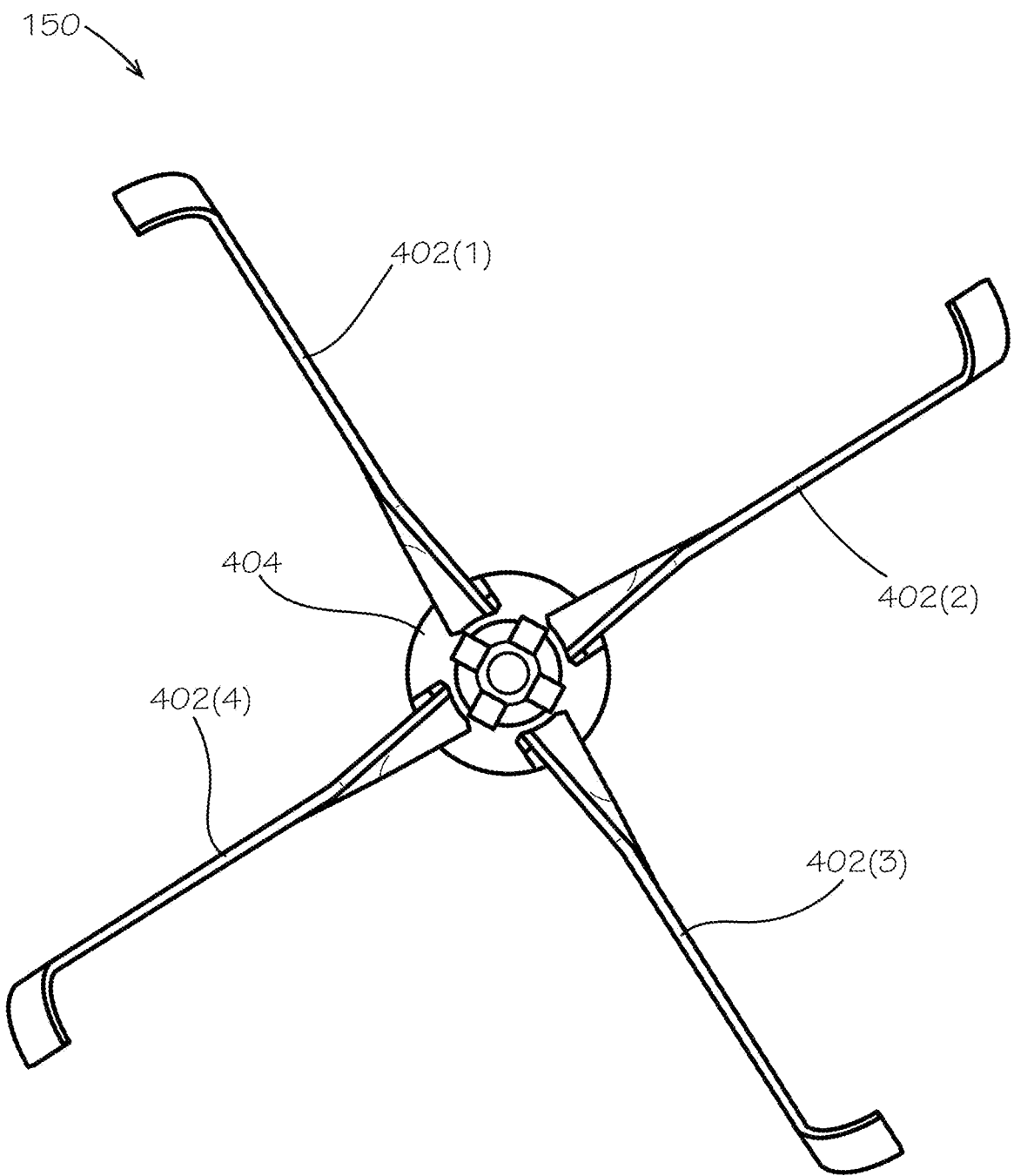
FIG. 4C is a bottom view illustrating one embodiment of an endoscopic clip.
Figure 4D:
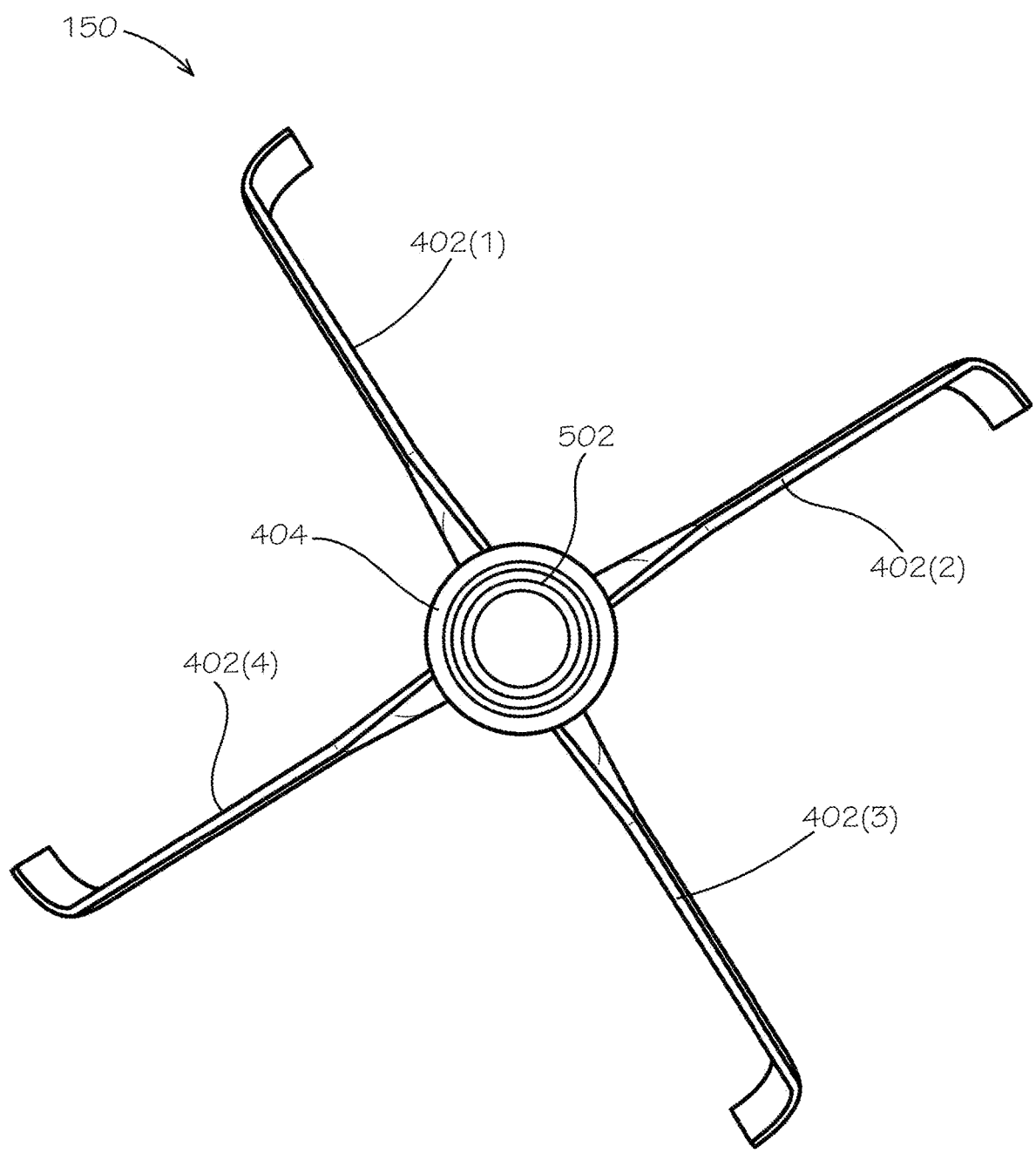
FIG. 4D is a top view illustrating one embodiment of an endoscopic clip.
Figure 5:
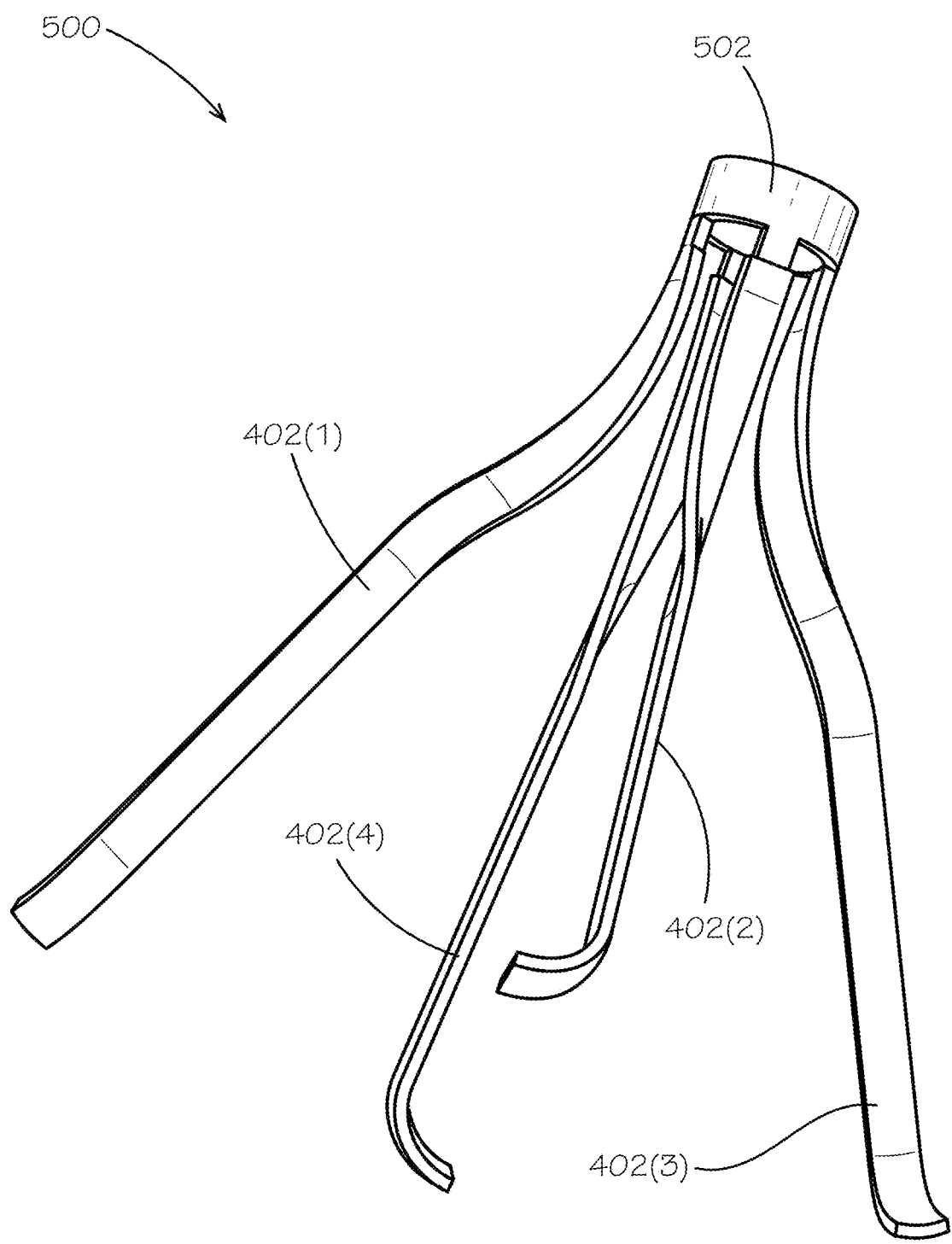
FIG. 5 is a perspective view illustrating one embodiment of an arm assembly of the endoscopic clip of FIGS. 4A-4D.

FIGS. 4A-4D depict various views of various embodiments of the endoscopic clip 150. In some embodiments, the endoscopic clip 150 may include one or more arms 402. For example, as depicted in FIGS. 4A-4D, the endoscopic clip 150 may include four arms 402(1)-(4). The endoscopic clip 150 may include one arm 402, two arms 402(1)-(2), three arms 402(1)-(3), four arms 402(1)-(4), or more than four arms 402(1)-(n). As depicted in FIG. 5, in some embodiments, one or more of the arms 402(1)-(n) may be disposed on an arm ring 502 in order to form an arm assembly 500. At least a portion of the arm assembly 500, such as the arm ring 502, may be disposed inside one or more other components of the endoscopic clip 150.

Returning to FIGS. 4A-4D, in one embodiment, the endoscopic clip 150 may include a mounting hub 404. The mounting hub 404 may include a tube-shaped assembly. As depicted in FIGS. 4A and 4C, the mounting hub 404 may include one or more slots. The slots may be disposed on the bottom of the mounting hub 404. The arm ring 502 of FIG. 5 may be disposed inside the mounting hub 404. One or more arms 402(1)-(n) may traverse through the one or more slots of the mounting hub 404. The one or more arms 402(1)-(n) may recede into the mounting hub 404 via the slots and may extend out of the mounting hub 404 via the slots. Further discussion of the mounting hub 404 is given below in relation to FIGS. 8A-8B.

As can be seen in FIG. 4A, in some embodiments, a center axis 406 may pass through the center of the endoscopic clip 150. As can also be seen from FIGS. 4A-4D, one or more arms 402(1)-(n) may be shaped to flare away from the center axis 406 in response to being at rest or in an extended position. As will be explained further below, the flaring of the one or more arms 402(1)-(n) and/or the helical shape of at least a portion of one or more of the arms 402(1)-(n) may cause the one or more arms 402(1)-(n) to be drawn together when retracted into the mounting hub 404, which may allow the endoscopic clip 150 to draw a wound closed.

Figure 6:
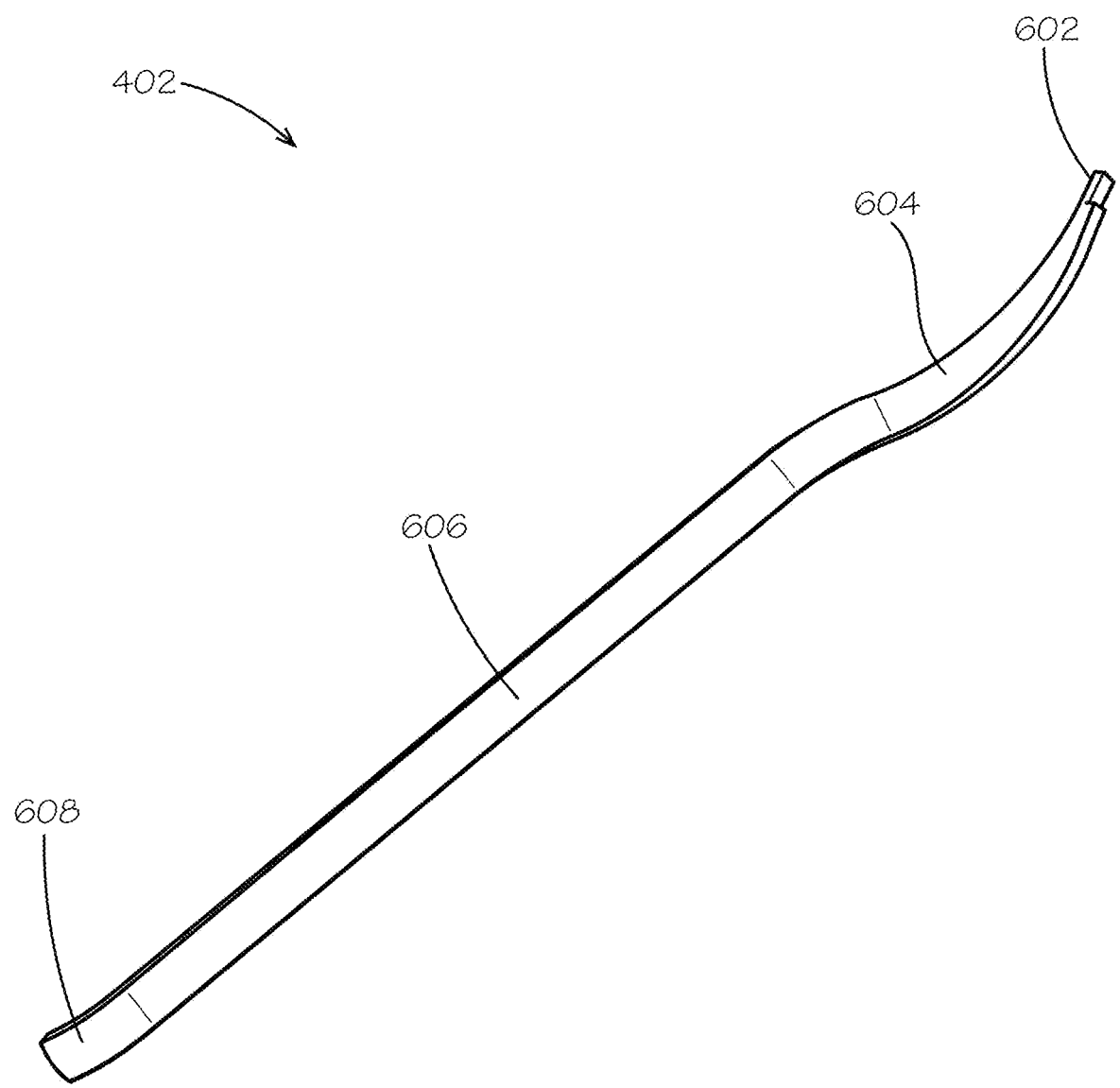
FIG. 6 is a perspective view illustrating one embodiment of an arm of the endoscopic clip of FIGS. 4A-4D.

FIG. 6 depicts one embodiment of an arm 402. The arm 402 may include a connection portion 602. The connection portion 602 may include the portion of the arm 402 that couples to the arm ring 502 or some other component of the apparatus 100. The arm 402 may include a helix portion 604. The helix portion 604 may include a portion of the arm 402 that may twist, turn, or form a helix shape. The arm 402 may include an extension portion 606. The extension portion 606 may include a portion of the arm 402 that extends downward from the helix portion 604. The extension portion 606 may include various lengths and shapes. For example, as depicted in FIG. 6, the extension portion 606 may be substantially straight, but in other embodiments, the extension portion 606 may twist along the axial length. In some embodiments, the arm 402 may include a distal end 608. The distal end 608 may include a portion of the arm 402 that may contact tissue or other material when the endoscopic clip 150 is in use. The distal end 608 may extend laterally from the arm 402. As depicted in FIG. 4C, the distal end 608 of multiple arms 402(1)-(n) may extend in the same direction (e.g., counter-clockwise when viewed from the bottom). In some embodiments, different distal ends 608 may face different directions from other distal ends 608. In one embodiment, a distal end 608 may face inward or outward. In some embodiments, the connection portion 602 and/or the helix portion 604 may be shaped such that the arm 402 may flare away from the center axis 406 when the arm 402 is extended out of a slot of the mounting hub 404.

Figure 7:
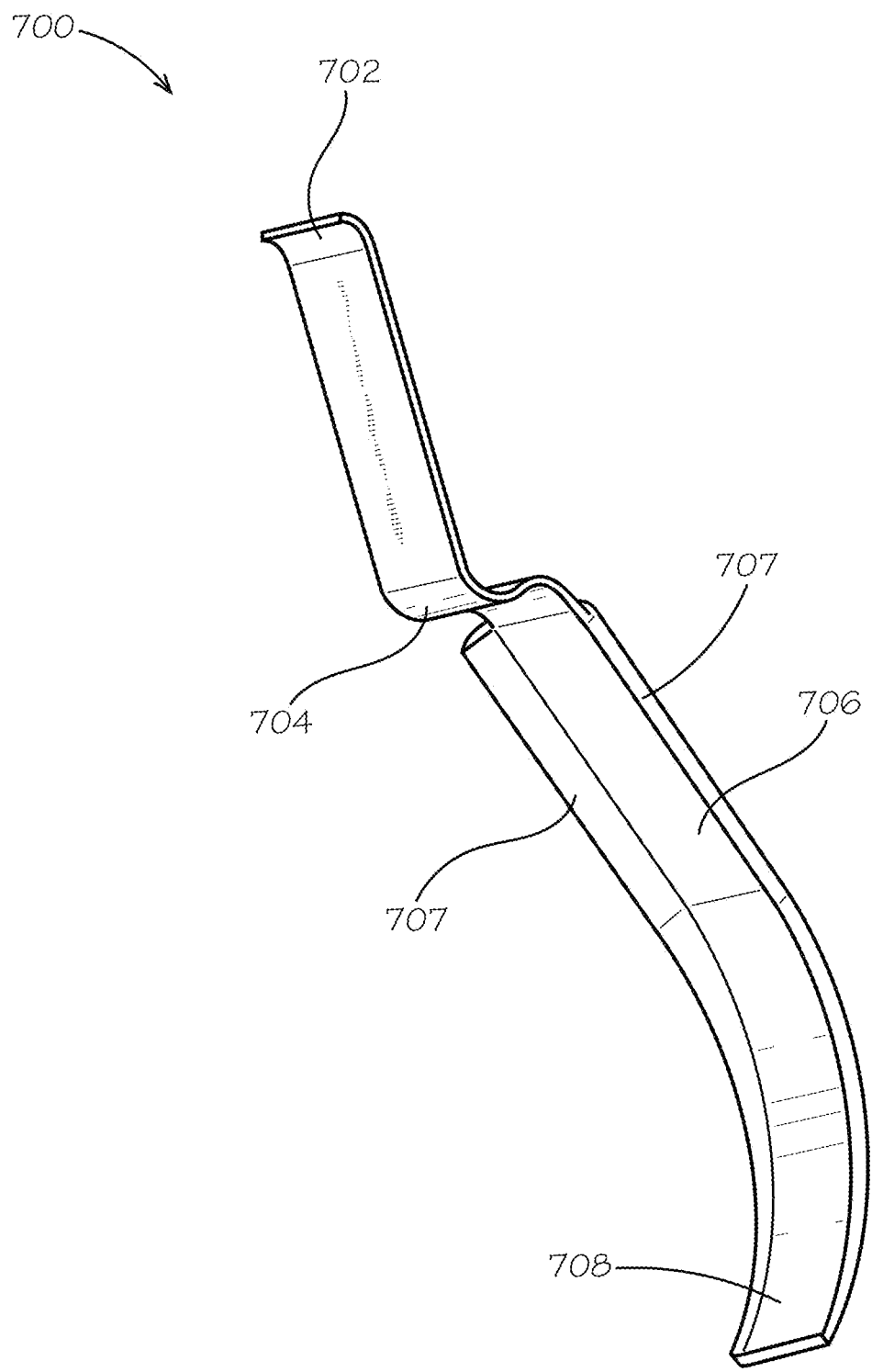
FIG. 7 is a perspective view illustrating another embodiment of an arm of an endoscopic clip.

FIG. 7 depicts one embodiment of an arm 700. The arm 700 may include a connection portion 702. The connection portion 702 may include the portion of the arm 700 that couples to the arm ring 502 or some other component of the apparatus 100. The arm 700 may include a bend portion 704. The bend portion 704 may include a portion of the arm 700 that forms a bend or elbow shape. The arm 700 may include an extension portion 706. The extension portion 706 may include a portion of the arm 700 that extends downward from the bend portion 704. The extension portion 706 may include various lengths or shapes. For example, as depicted in FIG. 7, the extension portion 706 may be substantially straight, but in other embodiments, the extension portion 706 may twist. The extension portion 706 may include one or more wing portions 707. The wing portion 707 may extend laterally from the extension portion 706. The wing portion 707 may extend at an angle from the extension portion 706. In some embodiments, the arm 700 may include a distal end 708. The distal end 708 may include a portion of the arm 700 that may contact tissue or other material when the endoscopic clip 150 is in use. The distal end 608 may extend laterally from the arm 402. As depicted in FIG. 7, the distal end 708 may extend toward an inside of the endoscopic clip 150.

In some embodiments, the endoscopic clip 150 may include multiple arms 402(1)-(n), and different arms 402 may include a different type of arm, whether of the type depicted in FIG. 6 or the type depicted in FIG. 7. In other embodiments, all of the arms 402 may be of the same type, i.e., all of the arms 402(1)-(n) may include the arm 402 depicted in FIG. 6 or all of the arms 402(1)-(n) may include the arm 700 depicted in FIG. 7.

Figure 8A:
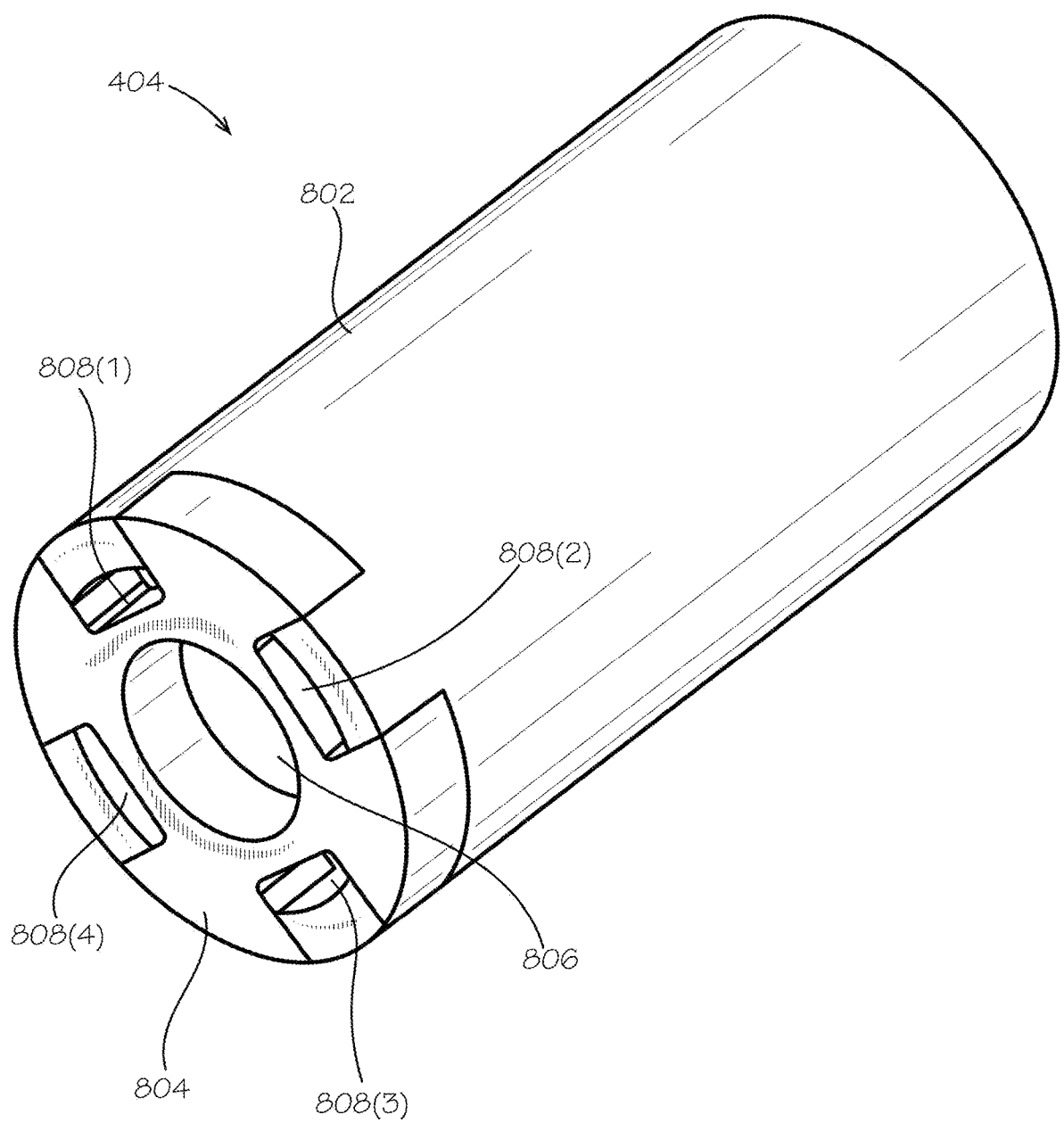
FIG. 8A is a perspective view illustrating one embodiment of a mounting hub of the endoscopic clip of FIGS. 4A-4D.
Figure 8B:
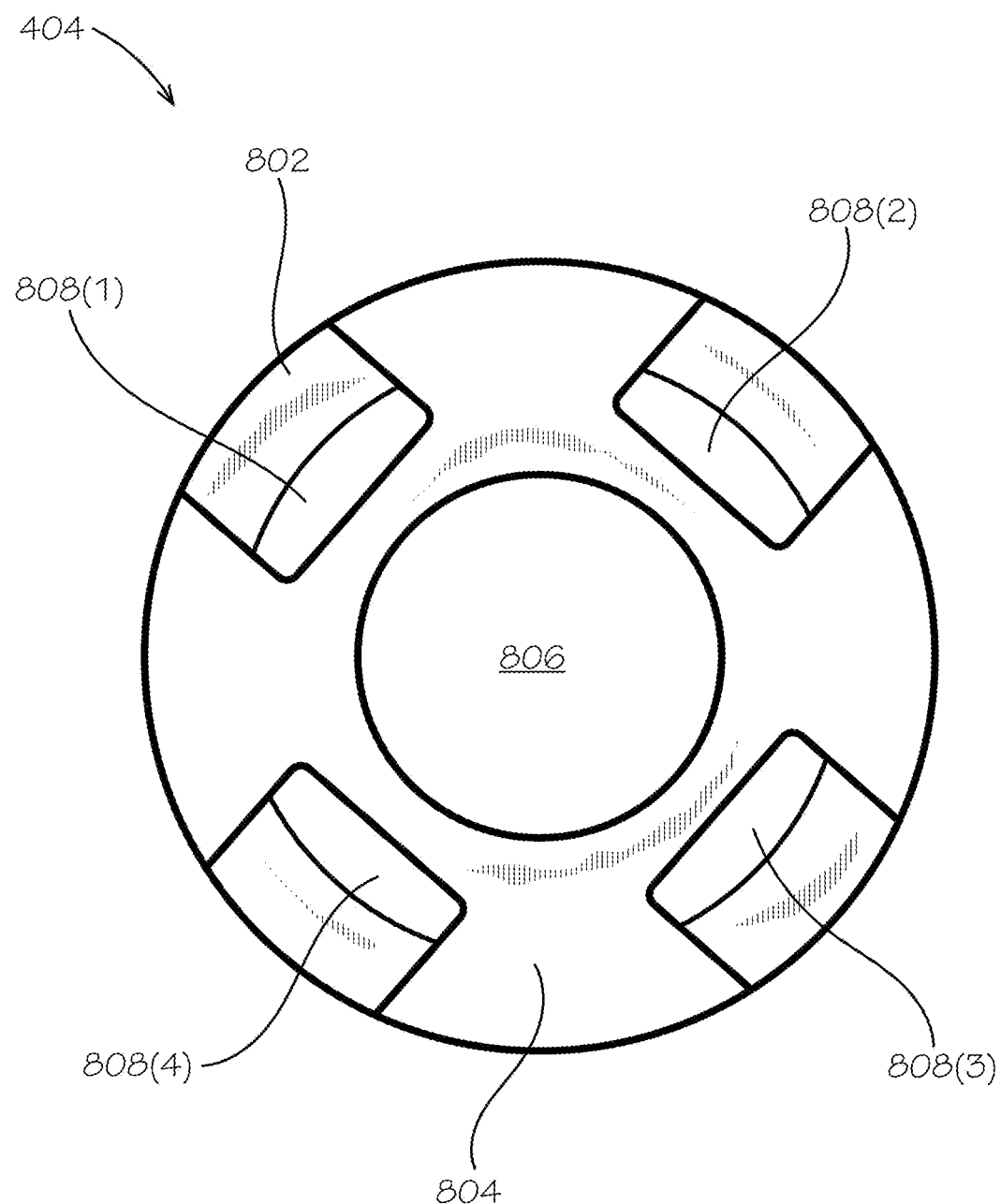
FIG. 8B is a bottom view illustrating another embodiment of the mounting hub of the FIG. 8A.

FIGS. 8A and 8B depict one embodiment of the mounting hub 404. The mounting hub 404 may include a duct 802. The duct 802 may include a container that may include an opening at one or both ends. The duct 802 may include a cylinder shape (as depicted in FIGS. 8A and 8B) or some other shape. The mounting hub 404 may include a bottom plate 804. The bottom plate 804 may include an aperture 806 that may allow access to the interior of the duct 802. In some embodiments, the mounting hub 404 may include one or more slots 808(1)-(n). A slot 808 may be formed in the duct 802, the bottom plate 804, or may be formed by the coupling of the duct 802 and the bottom plate 804. In some embodiments, a slot 808 may include a size or shape configured to be disposed around an arm 402. In one embodiment, the arm ring 502 may be disposed inside the duct 802. The arm ring 502 may translate up or down the interior of the duct 802.

Figure 9:
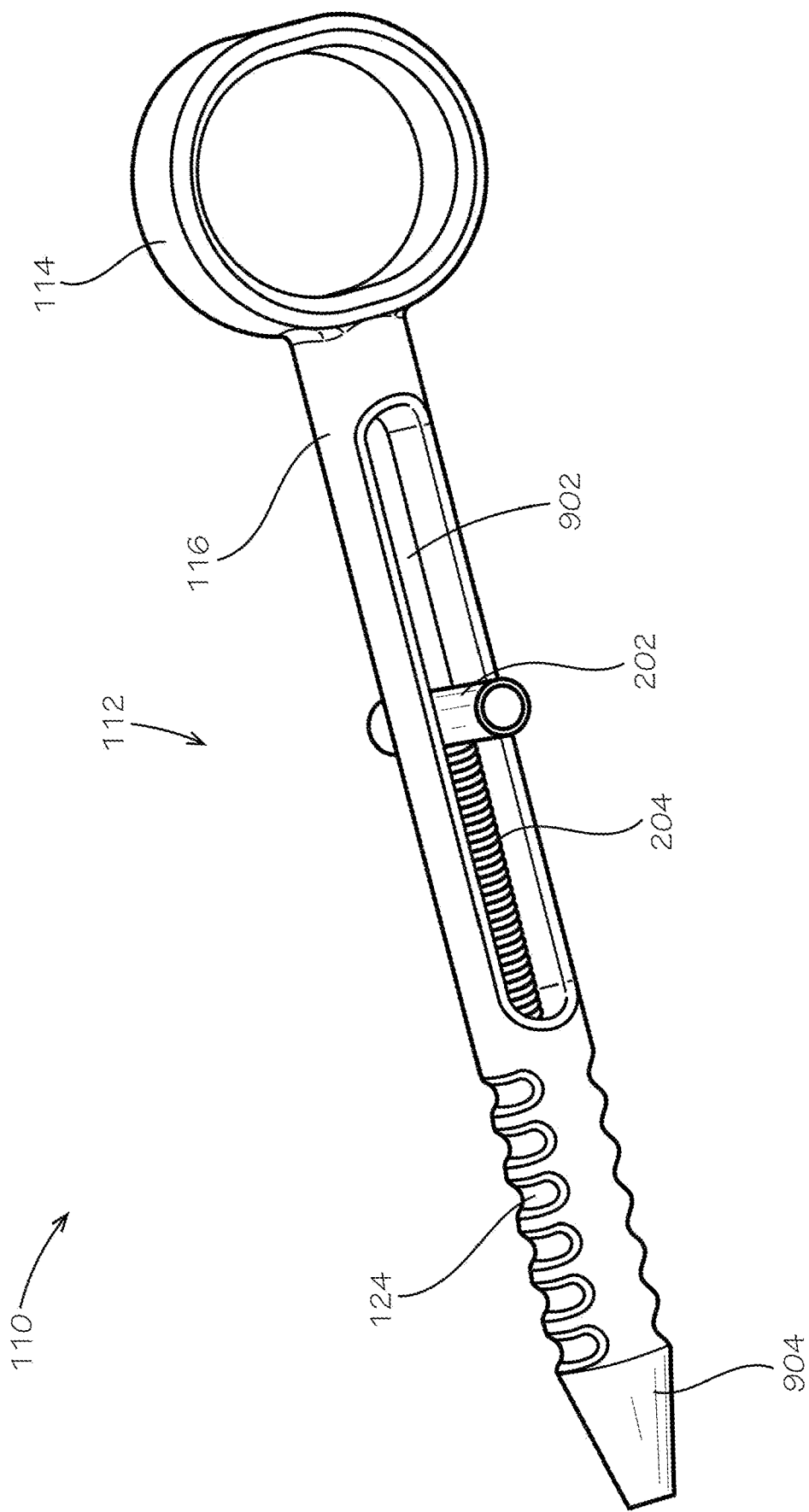
FIG. 9 is a perspective view illustrating one embodiment of a thumb pull of the apparatus for the endoscopic clip of FIG. 1.

FIG. 9 depicts one embodiment of certain components of the handle 110. As discussed above, the handle 110 may include the thumb pull 112, the loop 114, the shaft 116, and the ribbed structure 124. In one embodiment, the shaft 116 may include an aperture 902. The aperture 902 may include an aperture that runs along a length of a portion of the shaft 116. The spring clamp 202 may be disposed in the aperture 902. The spring clamp 202 may include a cylinder, bar, or other structure. The spring clamp 202 may be coupled to the stem 122 or the first or second stop 120(1)-(2) of the finger pull 118. In one embodiment, the spring 204 may be disposed in the aperture 902. The spring 204 may be coupled to the spring clamp 202. The spring 204 may couple to the shaft 116. In some embodiments, in response to the user of the apparatus 100 gripping the finger pull 118 and pulling on the loop 114, the spring 204 may compress. In some embodiments, the shaft 116 may include a distal end 904. The distal end 904 of the shaft 116 may be disposed on an opposite end of the handle 110 than the loop 114. In one embodiment, the tube 126 may penetrate through the distal end 904 of the shaft 116, and the tube 126 may couple to an interior portion of the shaft 116. In another embodiment, the tube 126 may couple to the distal end 904 of the shaft 116.

Figure 10:
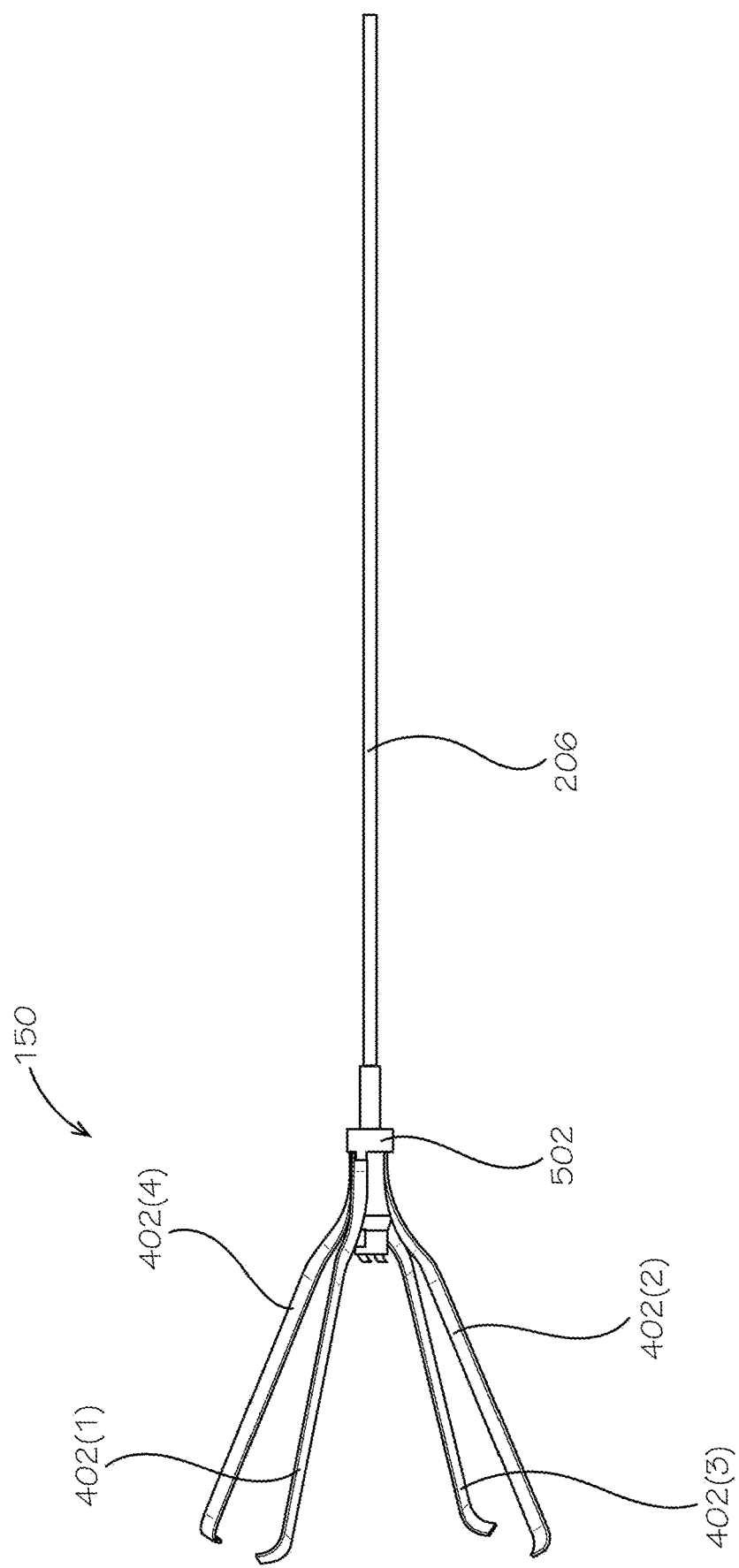
FIG. 10 is a side view illustrating one embodiment of an endoscopic clip and actuation wire of the apparatus for the endoscopic clip of FIG. 1.

FIG. 10 depicts one embodiment of certain components of the handle 110 and the endoscopic clip 150. The endoscopic clip 150 may include one or more arms 402(1)-(n) and the arm ring 502. In one embodiment, the actuation wire 206 may couple to the endoscopic clip 150. For example, as depicted in FIG. 10, the actuation wire 206 may couple to the arm ring 502. A portion of the actuation wire 206 may penetrate through the arm ring 502 and may couple to the arm ring 502. In some embodiments, a portion of the actuation wire 206 and the arm ring 502 may be disposed within the interior of the mounting hub 404. In one embodiment, the actuation wire 206 may be at least partially disposed within the tube 126. An end of the actuation wire 206 disposed opposite the end of the actuation wire 206 that couples to the endoscopic clip 150 may couple to the shaft 116.

In one embodiment, in response to the user of the apparatus 100 gripping the finger pull 118 of the handle 110 and pulling on the loop 114, the shaft 116 of the handle 110 may move toward the user. In response to the shaft 116 moving toward the user, the shaft 116 may pull on the actuation wire 206, which may be coupled to the shaft 116, and may move the actuation wire 206 toward the user. In response to the actuation wire 206 moving, the actuation wire 206 may open the one or more arms 402(1)-(n) wider than they may be when in a resting position. This may allow the one or more arms 402(1)-(n) to be able to engage with a larger wound. In response to the actuation wire 206 further moving, the actuation wire 206 may retract the one or more arms 402(1)-(n) inside the slots 808(1)-(n). In response to the helix portion 604 of the arm 402 engaging with the slot 808, the arm 402 may twist, cease to flare away from the center axis 406, and/or move toward the center axis 406 of the endoscopic clip 150. In response to the one or more arms 402(1)-(n) moving toward the center axis 406 of the endoscopic clip 150, the arms 402(1)-(2) may be drawn together. The user may execute this process so that the endoscopic clip 150 can engage with a wound in some tissue, close the wound, and hold the wound closed.

Figure 11A:
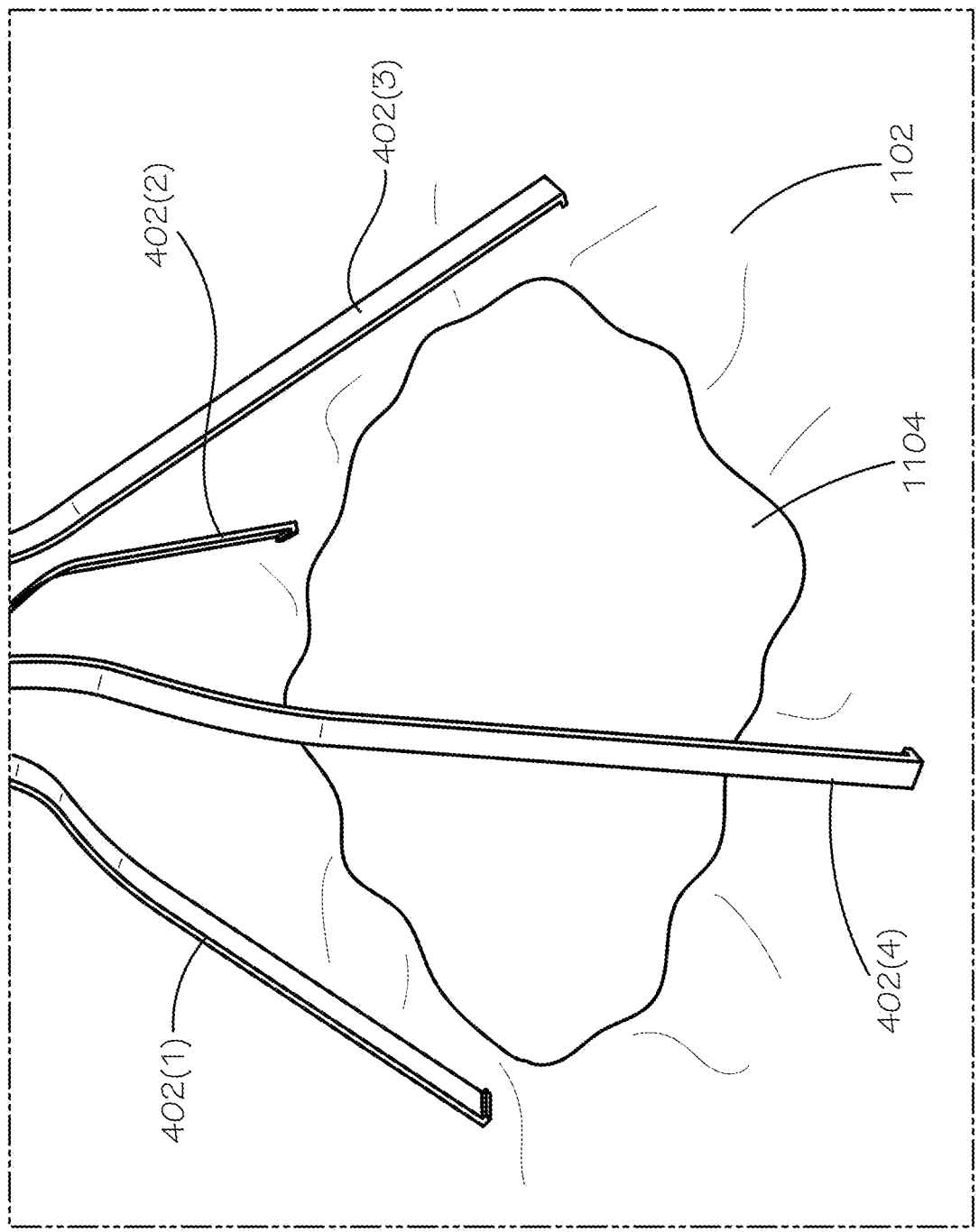
FIG. 11A is a perspective view illustrating one embodiment of a use of an apparatus for an endoscopic clip on a wound.
Figure 11B:
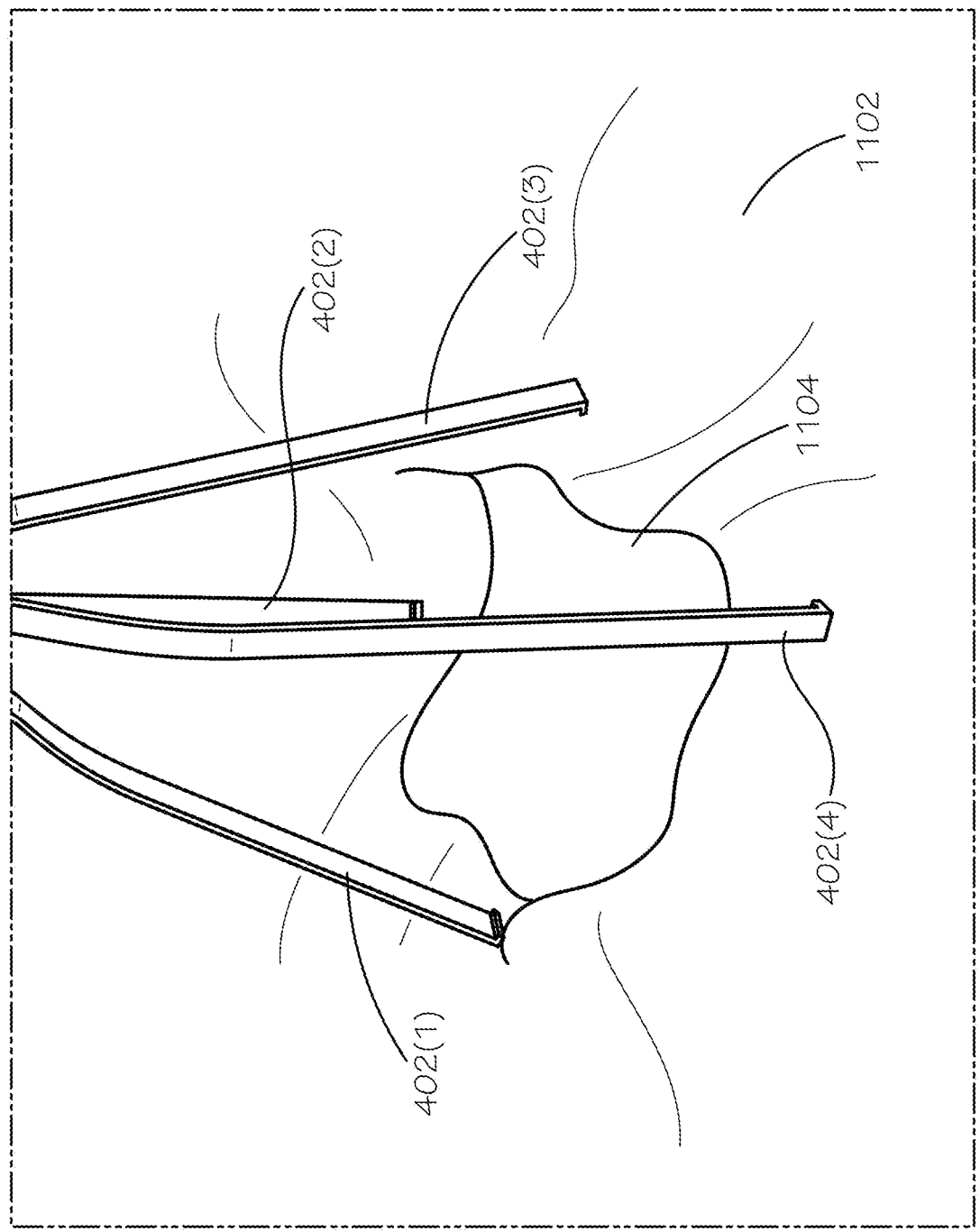
FIG. 11B is a perspective view illustrating another embodiment of a use of an apparatus for an endoscopic clip on a wound.
Figure 11C:
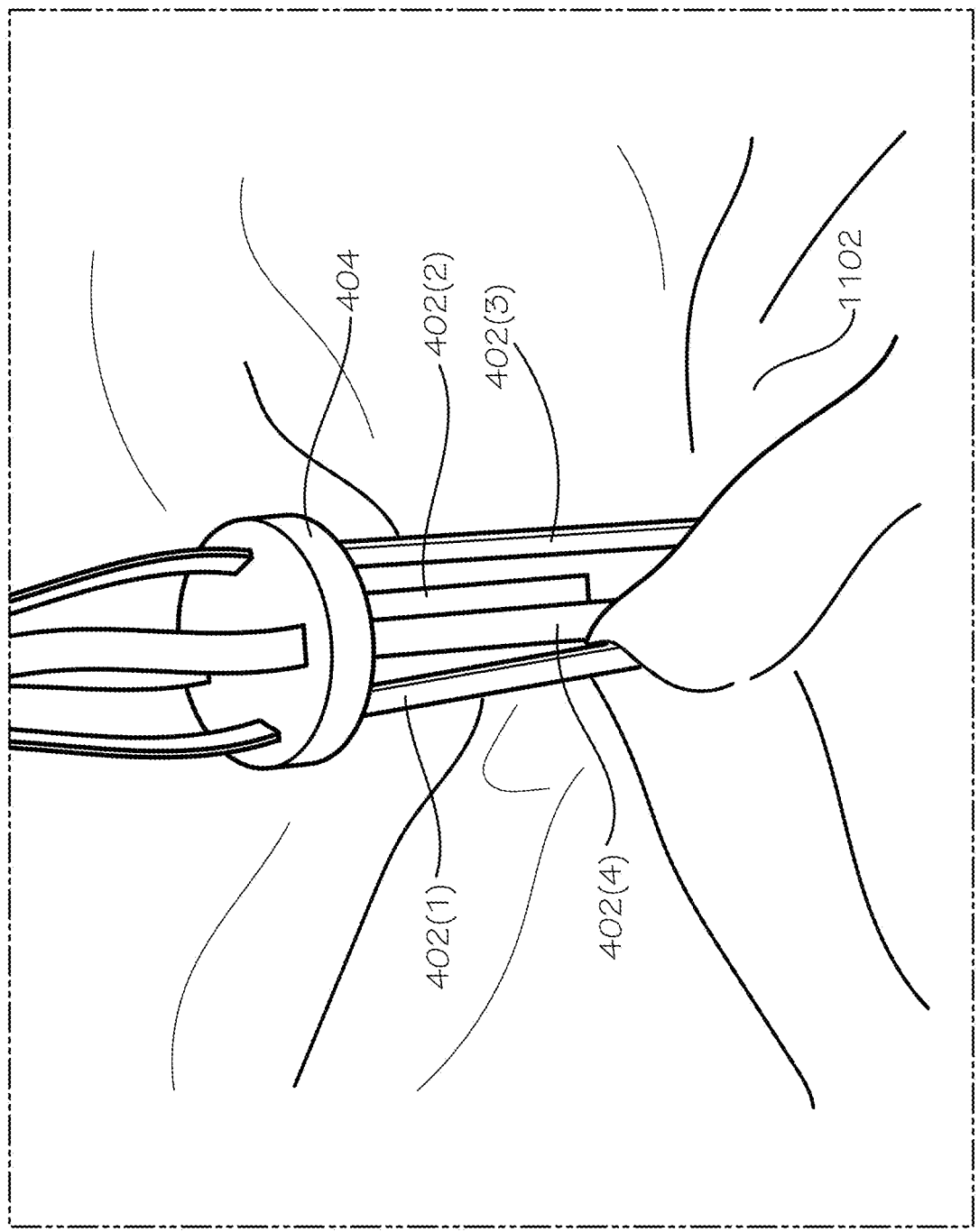
FIG. 11C is a perspective view illustrating another embodiment of a use of an apparatus for an endoscopic clip on a wound.

FIGS. 11A-11C depict an example wound closure using the endoscopic clip 150. As can be seen in FIG. 11A, a tissue 1102 may include a wound 1104, which may include a hole, incision, puncture, or some other type of wound. An endoscopic clip 150 may be disposed near the wound, and the arms 402(1)-(n) of the endoscopic clip 150 may be disposed around a perimeter of the wound 1104. In response to a user pulling on the loop 114 and eventually pulling on the actuation wire 206, the one or more arms 402(1)-(n) may open wider than their respective positions while at rest. A distal end 608 of each arm 402 may anchor the arm 402 into the tissue 1102 at multiple points along the perimeter of the wound 1104.

As can be seen in FIG. 11B, in response to a user further pulling on the handle 110 such that the actuation wire 206 further pulls the arms 402(1)-(n), the one or more arms 402(1)-(n) may retract into the mounting hub 404, and the helix portion 604 may engage with the slots 808 of the mounting hub 404. In response to such engagement, the one or more arms 404(1)-(n) may begin to rotate. The rotation of the one or more arms 402(1)-(n) may further engage the distal end 608 of each arm 402 with the tissue, which may grab the tissue 1102 for better engagement. The rotation of the one or more arms 402(1)-(n) may draw the one or more arms 402(1)-(n) together around the center axis 406 of the endoscopic clip 150.

As can be seen in FIG. 11C, the one or more arms 402(1)-(n) may be drawn together and may engage with each other. In response to the one or more arms 402(1)-(n) drawing together, the one or more arms 402(1)-(4) may draw the perimeter of the wound 1104 together to close the wound 1104.

In another embodiment where the arm 700 includes the configuration depicted in FIG. 7, in response to the user of the apparatus 100 gripping the finger pull 118 of the handle 110 and pulling on the loop 114, the shaft 116 of the handle 110 may move toward the user. In response to the shaft 116 moving toward the user, the shaft 116 may pull on the actuation wire 206, which may be coupled to the shaft 116, and may move the actuation wire 206 toward the user. In response to the actuation wire 206 moving, the actuation wire 206 may open the one or more arms 700(1)-(n) wider than they may be when in a resting position. This may allow the one or more arms 700(1)-(n) to be able to engage with a larger wound 1104. In response to the actuation wire 206 further moving, the actuation wire 206 may retract the one or more arms 700(1)-(n) inside the slots 808(1)-(n). In response to the bend portion 704 of the arm 402 engaging with the slot 808, the arm 700 may bend, cease to flare away from the center axis 406, and/or move toward the center axis 406 of the endoscopic clip 150. In response to the one or more arms 700(1)-(n) moving toward the center axis 406 of the endoscopic clip 150, the arms 700(1)-(2) may be drawn together. The user may execute this process so that the endoscopic clip 150 can engage with a wound in some tissue, close the wound, and hold the wound closed.

In one embodiment, the endoscopic clip 150 depicted herein may be able to close larger wounds 1104 with an overall shorter apparatus 100 than when compared to conventional endoscopic clips. The endoscopic clip 150 depicted herein may rely on the axial strength of the arms 402(1)-(n) to provide a tensile force that may pull tissue 1102 together rather than using flexural rigidity of the arms 402(1)-(n) to push the tissue 1102 as occurs in conventional endoscopic clips. In some embodiments, even if the resulting load does induce flexural buckling, the endoscopic clip 150 may still successfully close the wound 1104 because the distal ends 608 of the one or more arms 402(1)-(n) continue to draw the tissue 1102 together since the distal ends 608 may remain securely engaged with the initial anchoring sites on the tissue 1102.

In some embodiments, the apparatus 100 may form part of an endoscope. In some embodiments, the endoscopic clip 150 may be detachable from the remainder of the apparatus 100. This may allow the endoscopic clip 150 to remain in place and continue to hold a wound 1104 closed while the remainder of the apparatus 100 moves to another location or withdraws from the wound 1104 site.

Referring to FIGS. 12A-12D, additional embodiments of the present disclosure provide an endoscopic clip apparatus 100 including a clip 10 configured to engage and manipulate patient tissue, an actuation wire 70, a clip sleeve 50 configured to travel axially over the clip 10 to constrain and close the clip 10, and a catheter tube 80. Clip 10 includes a plurality of arms 12a, 12b, 12c, 12d extending distally from the clip sleeve 50. Arms 12 comprise a resilient material such as metal, and each arm may flex across a range of motion to engage tissue. During use, clip sleeve 50 may be advanced distally over clip 10 such that the interior of clip sleeve 50 constrains each arm 12, causing the distal ends of the arms 12 to advance toward the center longitudinal axis and close toward each other. Arms 12 are joined at a proximal end to a hub 14 in some embodiments. Hub 14 and the proximal ends of arms 12 are housed inside clip sleeve 50 during use. Clip sleeve 50 includes one or more proximal openings 50 to allow axial travel of clip sleeve 50 relative to clip 10.

A release joint 16 is disposed at the proximal end of clip 10, forming a detachable engagement between a control wire 70 and clip 10. Release joint 16 provides a mechanism for a user to separate clip 10 and clip sleeve 50 from a catheter tube 80 once the clip is closed in a desired position engaging patient tissue. Release joint 16 may include various embodiments for releasing clip 10 and clip sleeve 50 from catheter tube 80. In some embodiments, release joint 16 includes a ball 18 disposed at the distal end of control wire 70. Ball 18 is received in a socket 20 defined by first and second flanges 13a, 13b protruding from opposing arms proximally from hub 14. First and second flanges 13a, 13b are biased inwardly toward ball 18 such that first and second flanges 13a, 13b apply a compressive radial force against ball 18 to maintain ball 18 in socket 20. During use, control wire 70 may be translated axially in catheter tube 18 to advance or retract clip 10 inside the interior passage 54 formed by clip sleeve 50.

Figure 12D:
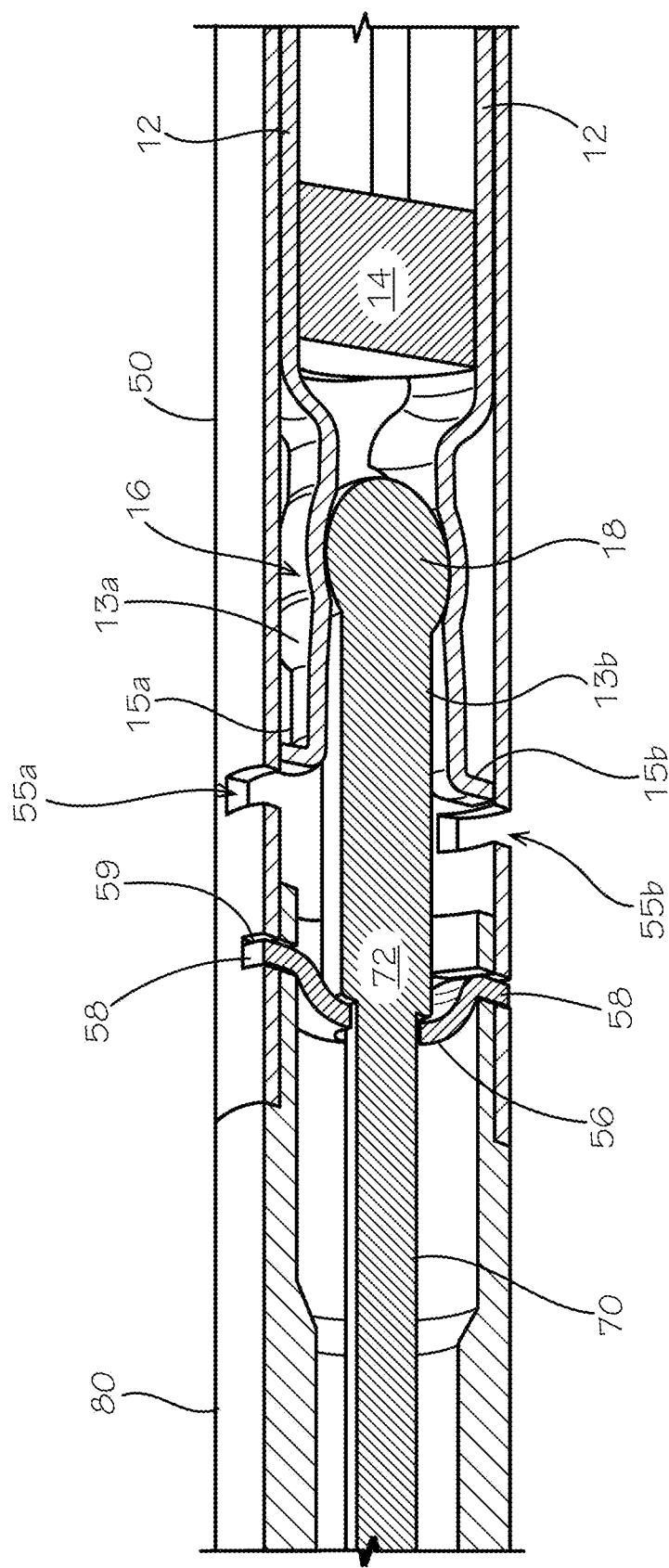
FIG. 12D is a detail partially exploded cross-sectional perspective view of an embodiment of an endoscopic clip apparatus including a release joint.

Referring to FIG. 12D, release joint 16 is shown inside the inner cavity in clip sleeve 50. When control wire 70 is retracted axially relative to catheter tube 80 and clip sleeve 50, release joint 16 approaches a release location near the proximal end of clip sleeve 50. First and second proximal flanges 13a, 13b each include a release pin 15a, 15b, respectively, projecting radially outwardly inside clip sleeve 50. Release pins 15a, 15b are biased radially outwardly, but are constrained radially inwardly due to the engagement with the inner wall of clip sleeve 50. As control wire 70 is retracted, release pins 15a, 15b approach and engage corresponding release pin sockets 55a, 55b in clip sleeve 50. Once aligned with the release pin sockets 55a, 55b, release pins 15a, 15b spring radially outwardly and enter the corresponding release pin sockets, thereby releasing the clamp on ball 18 and allowing control wire 70 to continue its axial travel in the proximal direction.

In addition to the release joint 16 disengaging the ball 18 from clip 10, a sleeve retainer 56 provides a detachable connection between the distal end of catheter tube 80 and clip sleeve 50. Sleeve retainer 56 includes a resilient clip housed inside catheter tube 80 and clip sleeve 50 at an overlapping joint. One or more retainer sockets 59 are defined through the sidewalls of catheter tube 80 and clip sleeve 50, and a sleeve retainer pin 58 extends through each retainer socket 59 to maintain engagement between catheter tube 80 and clip sleeve 50. When control wire 70 is retracted to a desired position, a shoulder 72 on control wire 70 is positioned to engage sleeve retainer 56. Further retraction of control wire 70 causes shoulder 72 to press against sleeve retainer 56, thereby deflecting each sleeve retainer pin 78 radially inwardly, thereby releasing the sleeve retainer and detaching the mechanical joint between catheter tube 80 and clip sleeve 50. In some embodiments, the device is configured such that shoulder 72 engages sleeve retainer 76 after release joint 16 is released. In other embodiments, the device is configured such that shoulder 72 engages sleeve retainer 76 simultaneously with the operation of release joint 16. In further embodiments, the device is configured such that shoulder 72 engages sleeve retainer 76 before the release joint 16 is released.

Figure 13:
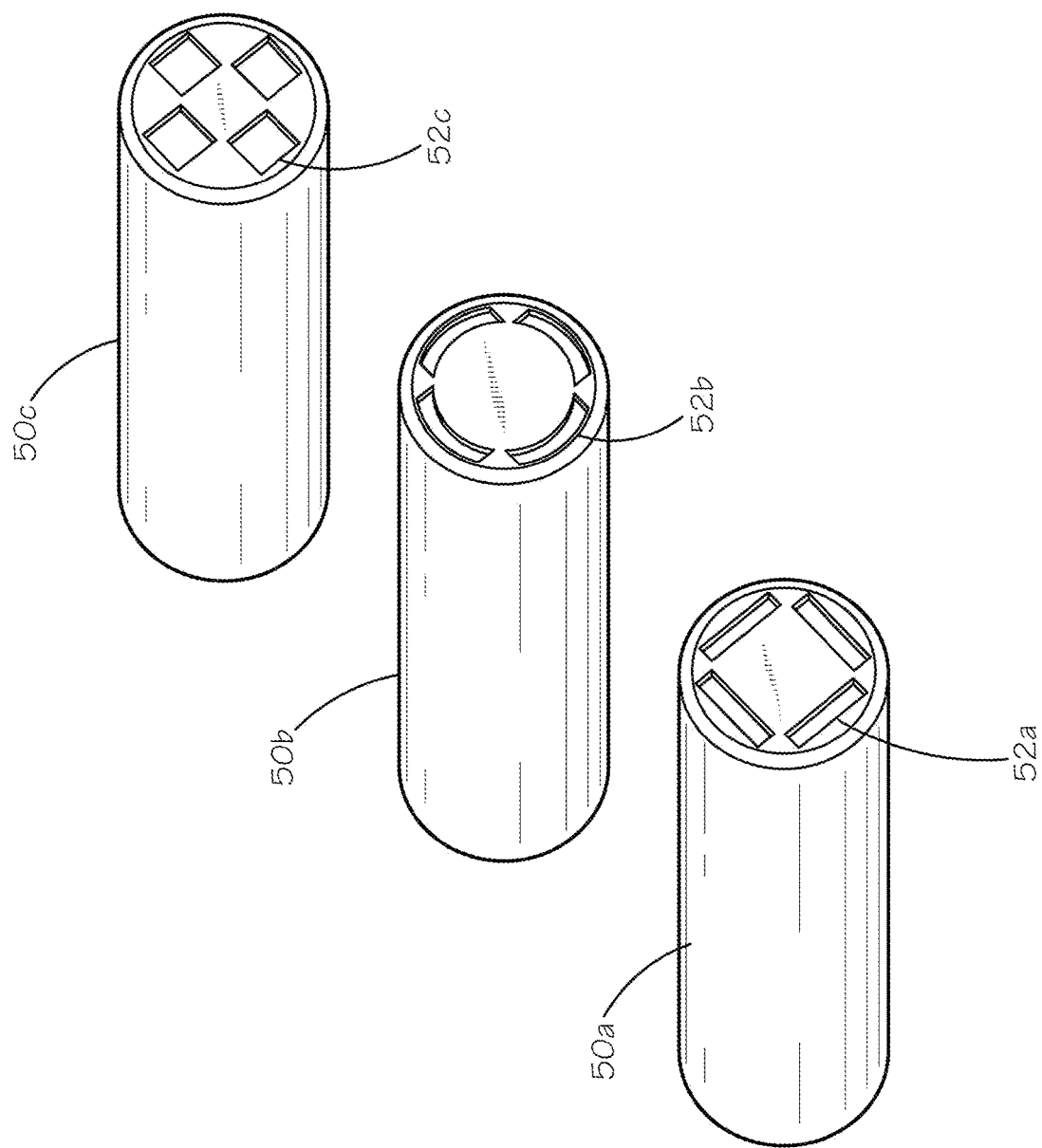
FIG. 13 is a perspective view showing embodiments of a clip sleeve for an endoscopic clip apparatus.

Referring to FIG. 13, clip sleeve 50 may include various embodiments depending on the configuration of the arms disposed in the device. Clip sleeve 50a is configured in some embodiments with a plurality of rectangular distal openings 52a defined in the distal end wall. Each rectangular distal opening 52a is shaped to accommodate and constrain an arm on the clip having a rectangular cross-sectional profile. Clip sleeve 50b is configured in some embodiments with a plurality of curvilinear distal openings 52b. Each curvilinear distal opening 52b is shaped to accommodate and constrain an arm on the clip having a corresponding curvilinear cross-sectional profile. Clip sleeve 50c is configured in some embodiments with a plurality of square distal openings 52c defined in the distal end wall. Each square distal opening 52c is shaped to accommodate and constrain an arm on the clip having a corresponding square cross-sectional profile. Numerous other polygonal or curvilinear distal openings may be provided to accommodate clip arms having corresponding cross-sectional shapes.

Figure 14A:
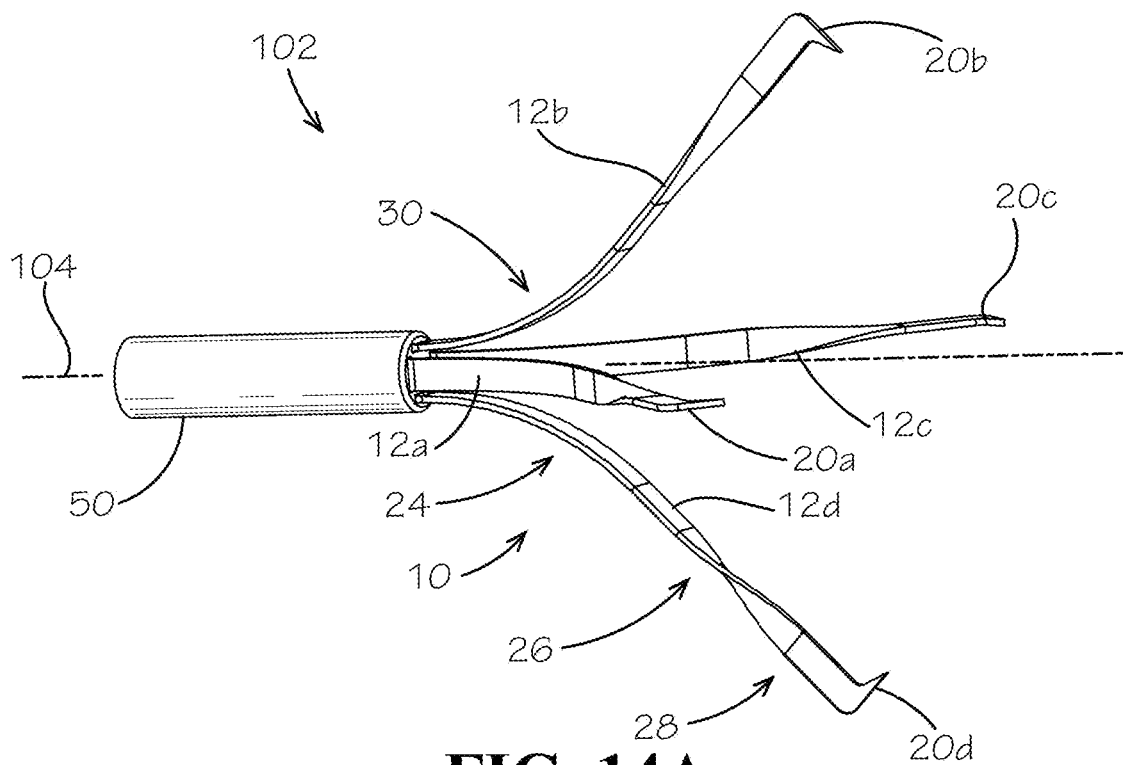
FIG. 14A is a perspective view of an embodiment of an endoscopic clip apparatus in a deployed position.
Figure 14B:
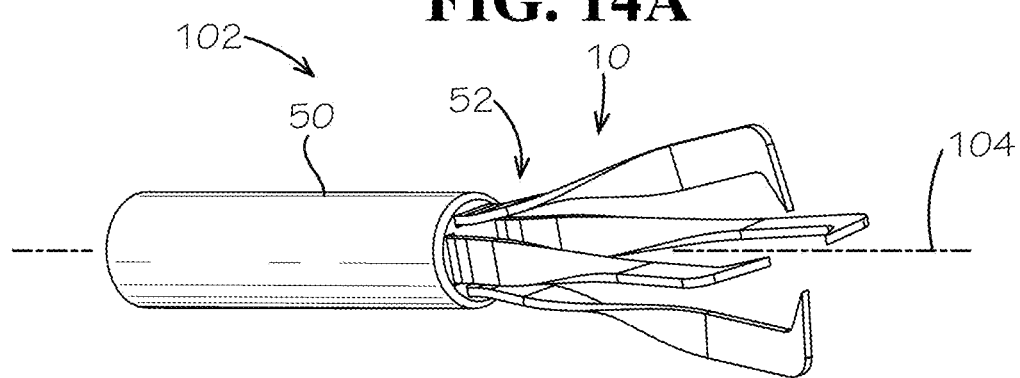
FIG. 14B is a perspective view of an embodiment of an endoscopic clip apparatus in a partially retracted position.
Figure 14C:
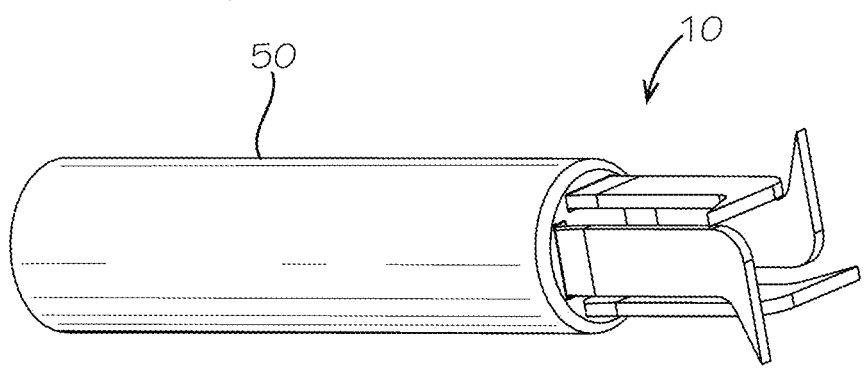
FIG. 14C is a perspective view of an embodiment of an endoscopic clip apparatus in a retracted position.

Referring to FIGS. 14A-14C, an embodiment of a detachable clip apparatus 102 includes a clip 10 and a clip sleeve 50. Clip 10 is configured to be advanced or retracted axially relative to clip sleeve 50 to constrain or deploy the clip. As shown in FIG. 14A, clip 10 is shown in an open, or deployed, position with the clip arms 12a, 12b, 12c, 12d extending away from the longitudinal axis 104. Each clip arm includes a distal arm tip 20a, 20b, 20c, 20d. The distal arm tips 20a, 20b, 20c, 20d may include different shapes to provide optimized engagement with patient tissue during a procedure. For example, as shown in FIGS. 14A-14C, distal arm tips 20a, 20b, 20c, 20d each include a square distal end with a triangular point projecting radially inwardly toward longitudinal axis 104 when the arms are in the deployed position.

Each clip arm 12a, 12b, 12c, 12d includes three lengthwise sections in some embodiments. A proximal first section 24 includes a uniform cross-section with no twist profile in some embodiments. A middle second section 26 includes an axially twisted profile. The axially twisted profile includes a twist about the longitudinal axis of the arm. The axial twist may be formed in the shape of a spiral or helical twist in some embodiments. The rate of twist, location of twist and total twist angle may be varied from arm to arm to achieve desired performance objectives. A third distal section 28 includes a uniform cross-section with no twist profile in some embodiments.

When clip 10 is initially retracted relative to clip sleeve 50, as shown in FIG. 14A and FIG. 14B, the proximal first section 24 of each clip arm 12a, 12b, 12c, 12d travels through a corresponding distal opening 52 in clip sleeve 50. During travel of the proximal first section 24, each arm moves radially inwardly toward longitudinal axis 104 due to the closing radius 30 defined in each clip arm. The closing radius 30 comprises a curvature profile on each clip arm such that each arm is constrained and forced toward longitudinal axis 104 as clip 10 is retracted relative to clip sleeve 50. However, due to the non-twisted profile of the proximal first sections 24 of each clip arm, each clip arm does not twist during the first stage of retraction along the proximal first sections 24.

During a second stage of retraction, the middle second sections 26 of each clip arm 12a, 12b, 12c, 12d travels through distal opening 52 in clip sleeve 50. As the middle second sections 26 of each clip arm travels into clip sleeve 50, each arm twists according to the axial twist profile of the middle second section 26. This axial twisting action causes the distal tips 20a, 20b, 20c, 20d on each clip arm 12a, 12b, 12c, 12d to rotate, thereby enhancing the grasping engagement with tissue as the clip closes toward the longitudinal axis 104. Thus, the clip 10 is configured to simultaneously advance each arm toward longitudinal axis 104 and to axially twist each arm during closure to provide both a grasping and cinching motion on the patient tissue during closure of the clip 10.

As shown in FIG. 14C, the third stage of retraction includes travel of the distal third sections 28 of each arm into clip sleeve 50. Because each distal third section 28 includes a substantially flat profile, the arms do not twist during this final stage of retraction in some embodiments.

Figure 15A:
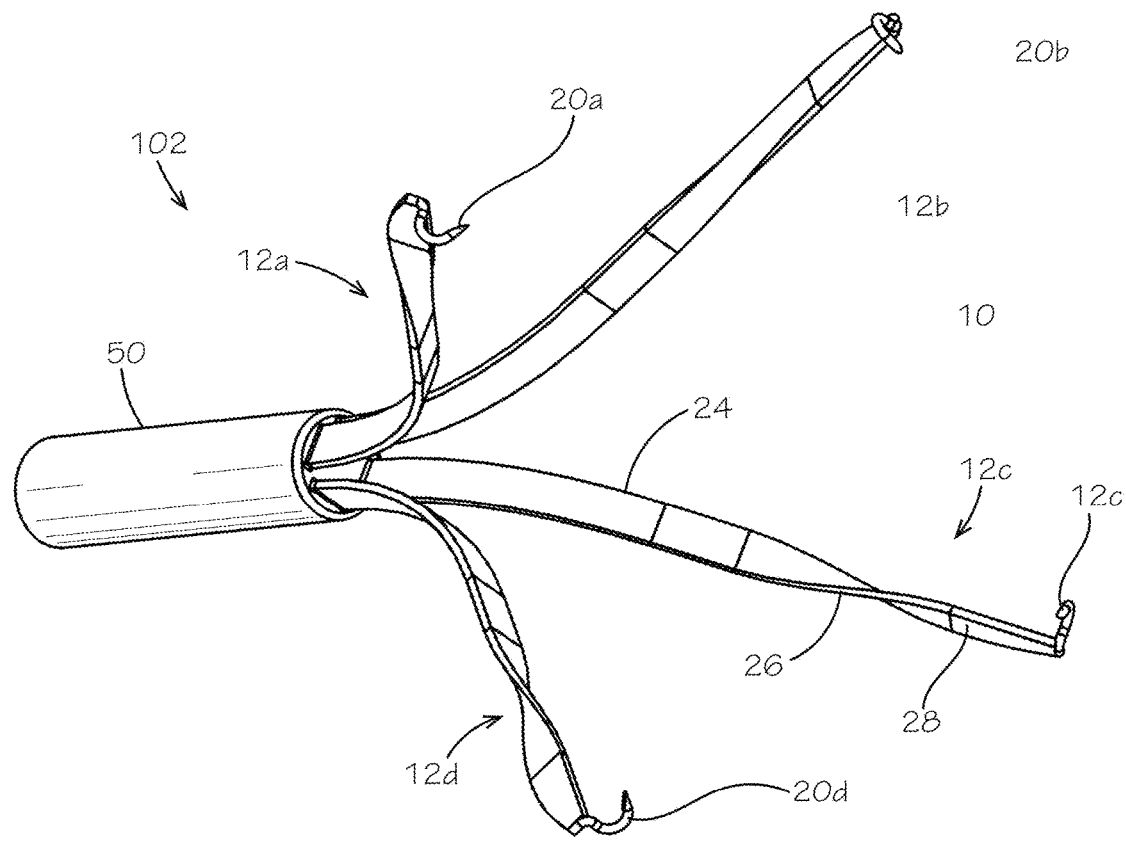
FIG. 15A is a perspective view of an embodiment of an endoscopic clip apparatus in a deployed position.
Figure 15B:
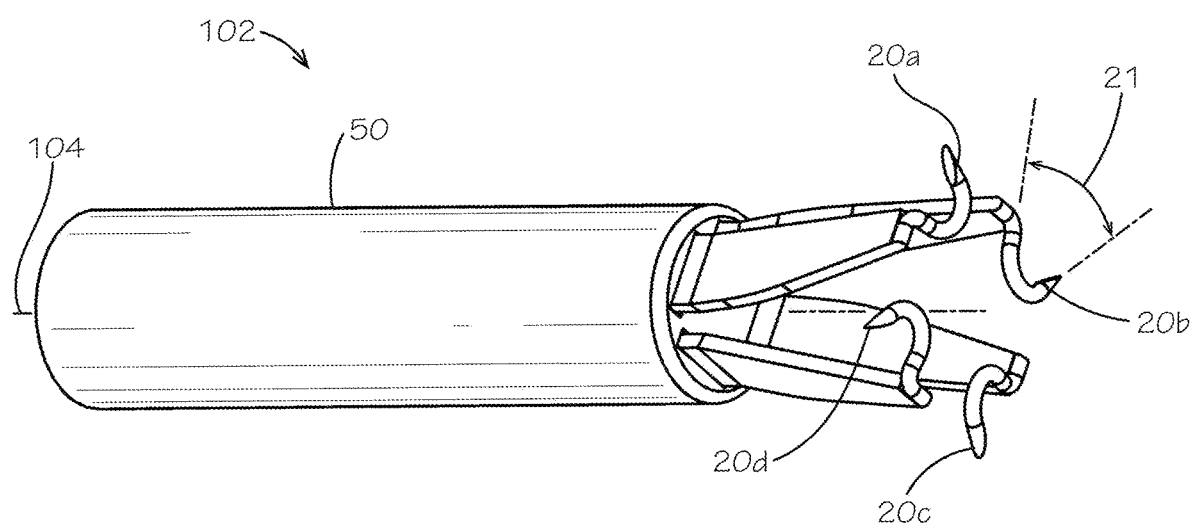
FIG. 15B is a perspective view of an embodiment of an endoscopic clip apparatus in a partially retracted position.

Referring to FIGS. 15A and 15B, an additional embodiment of a detachable clip apparatus 102 includes a clip 10 and a clip sleeve 50. Clip 10 includes a plurality of clip arms 12a, 12b, 12c, 12d each including a distal tip 20a, 20b, 20c, 20d with a hook. In some embodiments, each hook includes a hook angle 21 less than ninety degrees. As such, each hook on each distal tip is oriented pointing away from longitudinal axis 104 when clip 10 is retracted, as shown in FIG. 15B.

Figure 16A:
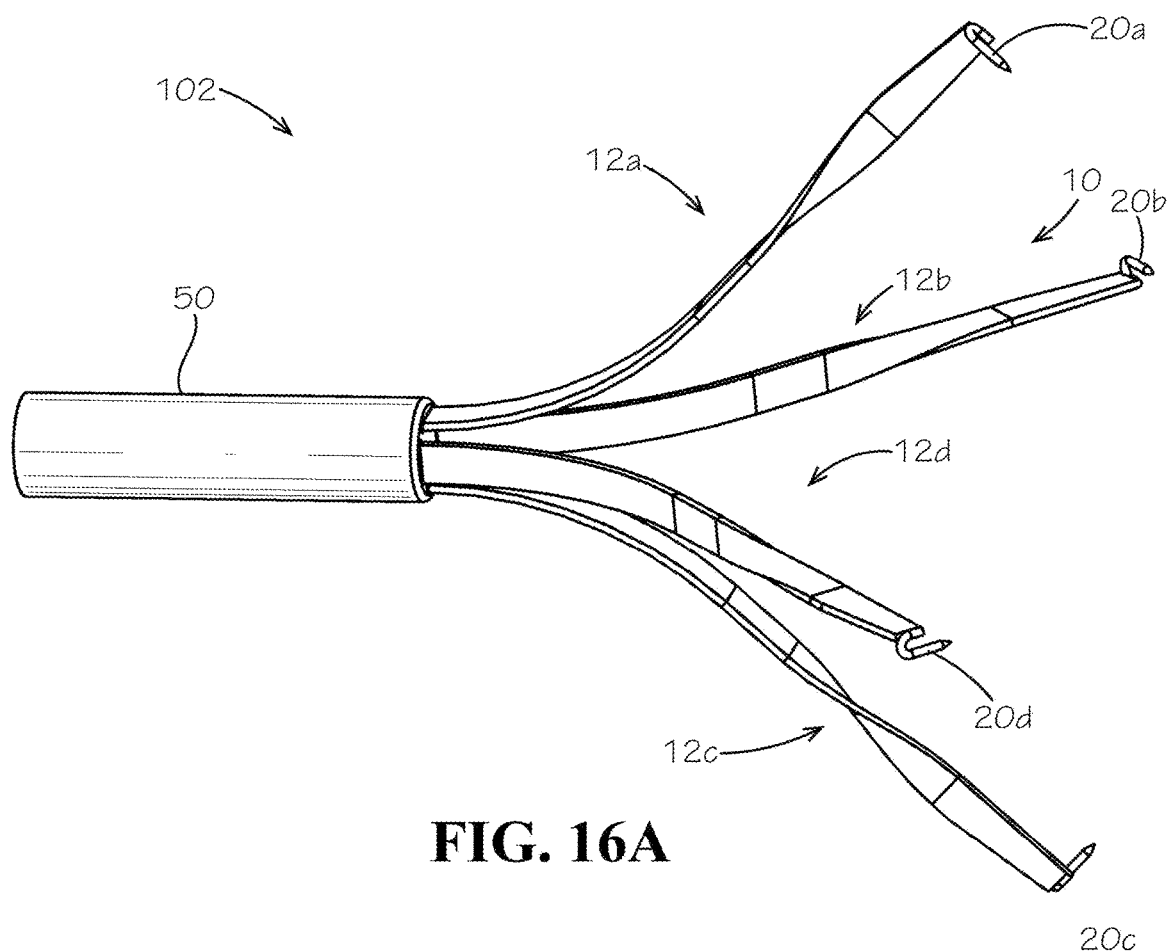
FIG. 16A is a perspective view of an embodiment of an endoscopic clip apparatus in a deployed position.
Figure 16B:
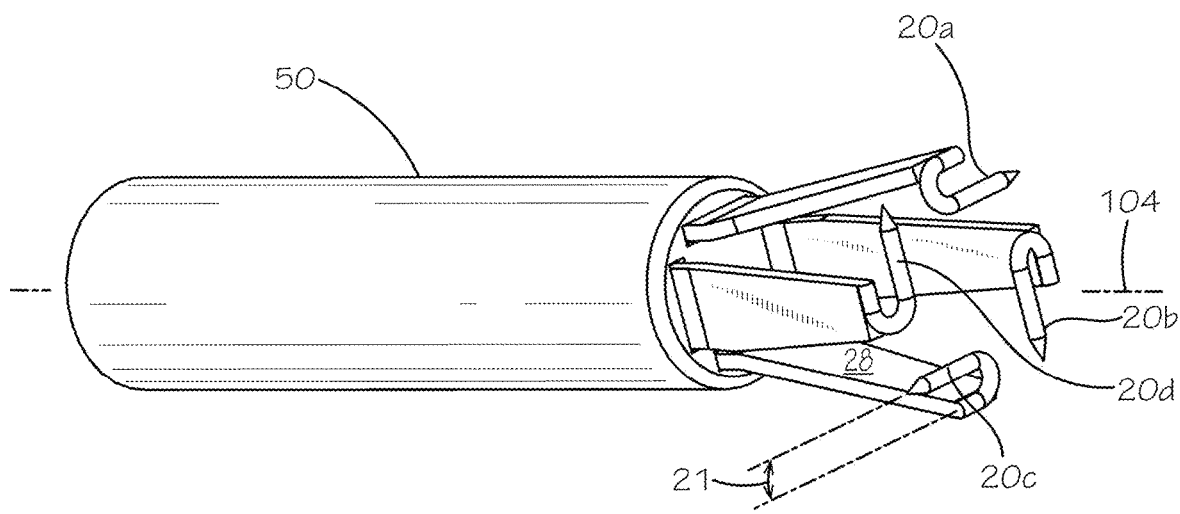
FIG. 16B is a perspective view of an embodiment of an endoscopic clip apparatus in a partially retracted position.

Referring to FIG. 16A and FIG. 16B, an additional embodiment of a detachable clip apparatus 102 includes a clip 10 and a clip sleeve 50. Clip 10 includes a plurality of clip arms 12a, 12b, 12c, 12d each including a distal tip 20a, 20b, 20c, 20d with a hook having a hook angle 21 of about zero degrees such that the point of the hook on distal tip 20 is substantially parallel to the plane of distal third section 28 on each arm, and each point extends away from longitudinal axis 104 when clip is in the retracted position. Additionally, each hook is positioned on each arm such that the hook is closer to longitudinal axis 104 than the arm when retracted, as shown in FIG. 16B.

Figure 17A:
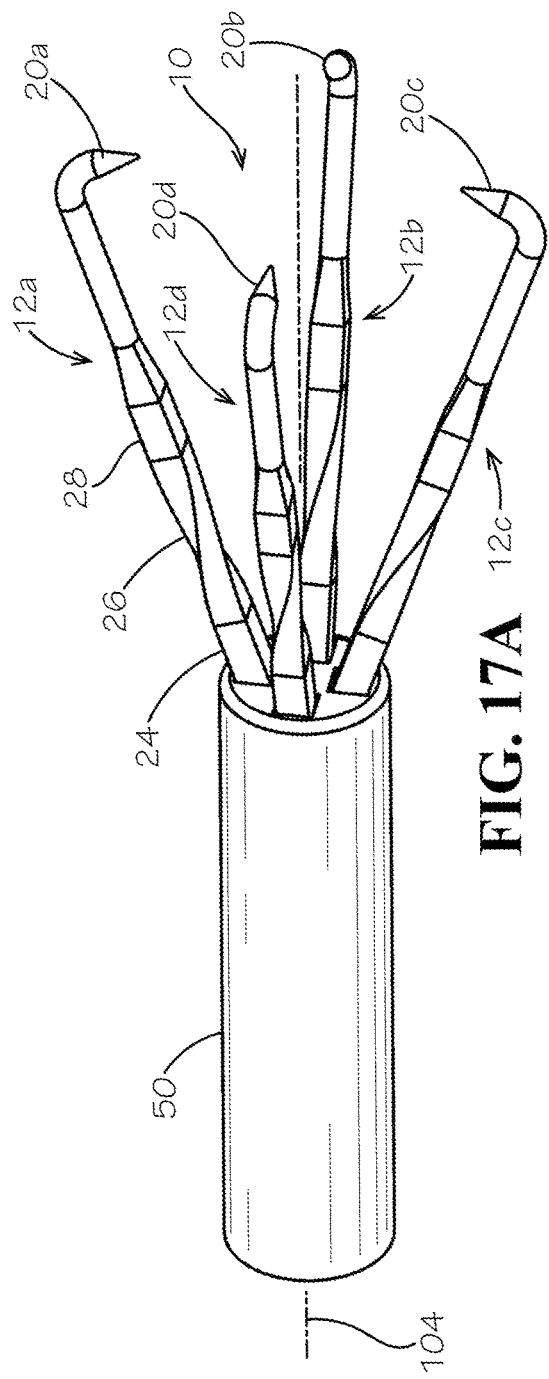
FIG. 17A is a perspective view of an embodiment of an endoscopic clip apparatus in a deployed position.
Figure 17B:
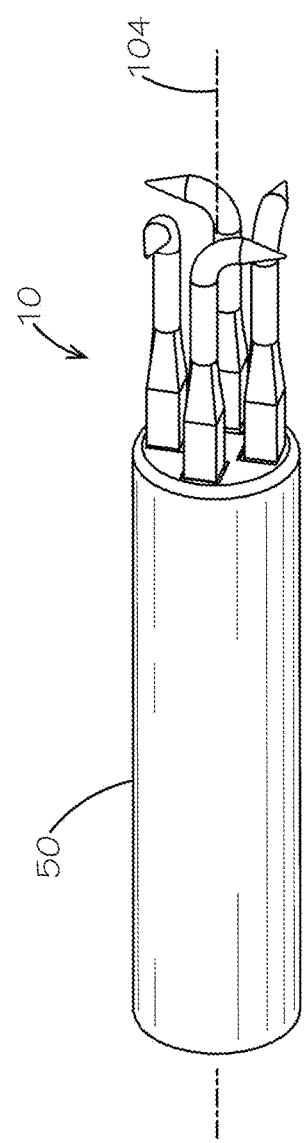
FIG. 17B is a perspective view of an embodiment of an endoscopic clip apparatus in a partially retracted position.

Referring to FIGS. 17A and 17B, an additional embodiment of a detachable clip apparatus 102 includes a clip 10 and a clip sleeve 50. In this embodiment, each arm 12a, 12b, 12c, 12d on clip 10 includes a substantially square cross-sectional shape. Each arm includes a first distal section 24, a middle section 26 and a distal section 28. The middle section 26 on each arm includes an axial twist of between zero and ninety degrees along the length of the arm in some embodiments. In some embodiments, the axial twist is about ninety degrees. Each arm includes a distal tip 20a, 20b, 20c, 20d including a point oriented toward longitudinal axis 104 when clip 10 is in the deployed positions, as shown in FIG. 17A. During retraction, each arm is constrained by clip sleeve 50, and each arm closes toward longitudinal axis 104 and also axially twists about ninety degrees, as shown in FIG. 17B, causing the distal tips to point away from and tangential to longitudinal axis 104. In some embodiments, the axial twist rate is constant along the twist section. In further embodiments, the rate of axial twist varies along the length of the twist section.

Figure 19A:
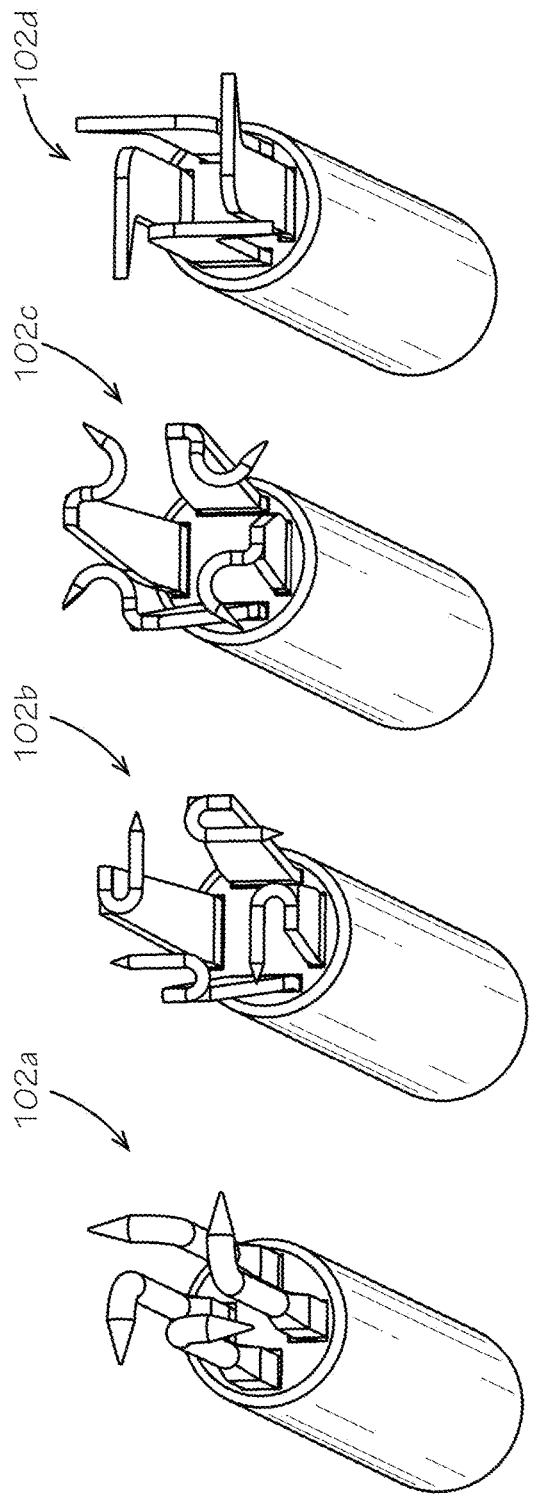
FIG. 19A is a perspective view showing different embodiments of distal tips for an endoscope clip.
Figure 19B:
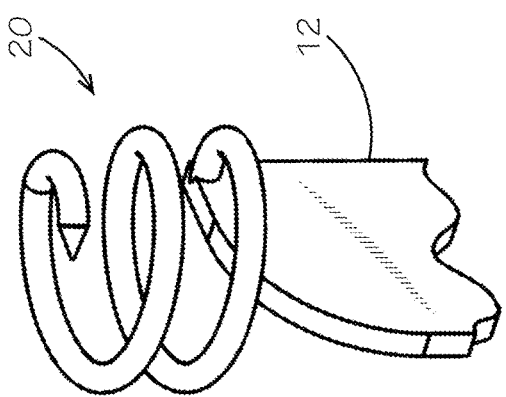
FIG. 19B is a perspective view of an embodiment of a distal tip of an endoscopic clip.
Figure 20A:
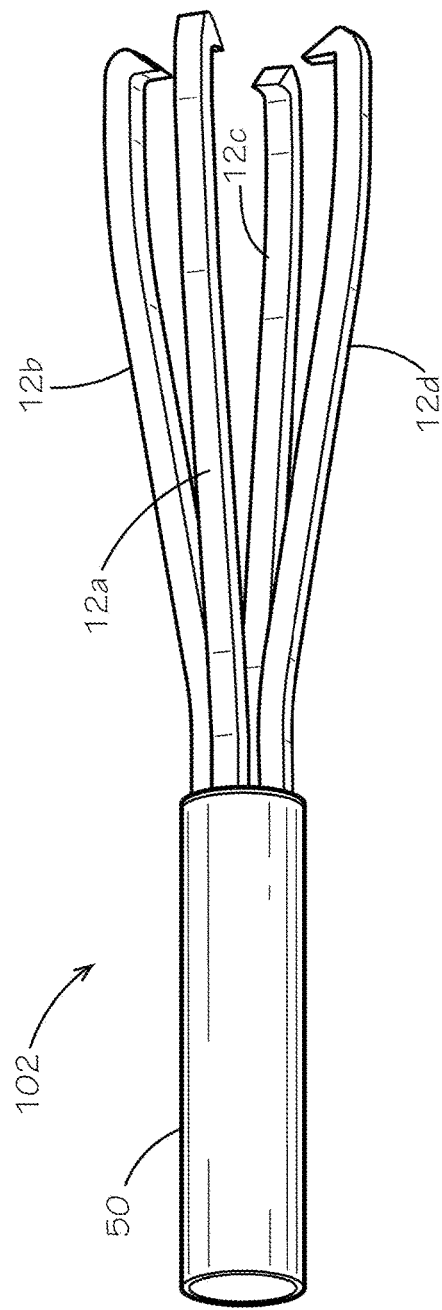
FIG. 20A is a perspective view of an embodiment of an endoscopic clip apparatus in a partially retracted position.
Figure 20B:
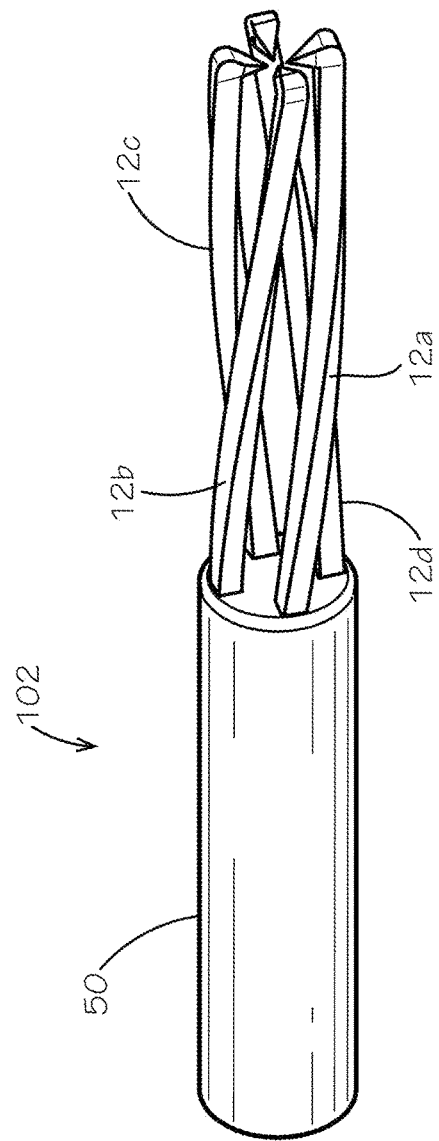
FIG. 20B is a perspective view of an embodiment of an endoscopic clip apparatus in a partially retracted position.

Referring to FIGS. 18A and 18B, an additional embodiment of a detachable clip apparatus 102 includes a clip 10 and a clip sleeve 50. In this embodiment, each arm includes a proximal first section 24, a middle second section 26 and a distal third section 28. Proximal first section 24 includes a substantially flat portion. Middle second section 26 includes an axial twist of about one-hundred-eighty degrees over an axial length less than the length of the clip sleeve 50. Distal third section 28 includes a substantially flat portion aligned angularly with the proximal first section 24. Each arm includes a distal tip 20a, 20b, 20c, 20d including a flange oriented substantially toward longitudinal axis 104 when clip 10 is in the deployed position, as shown in FIG. 18A. When clip 10 is retracted, each arm rotates one-hundred-eighty degrees, as shown in FIG. 18B, such that each flange is oriented substantially away from the longitudinal axis 104. Referring to FIG. 19A, various embodiments of detachable clip apparatuses 102a, 102b, 102c, 102d are shown. An alternative embodiment of a distal tip 20 of an arm 12 includes a spiral hook including at least two complete spiral turns, terminating at a point. Numerous other embodiments of distal tips configured for engagement with patient tissue may be included.

Figure 21A:
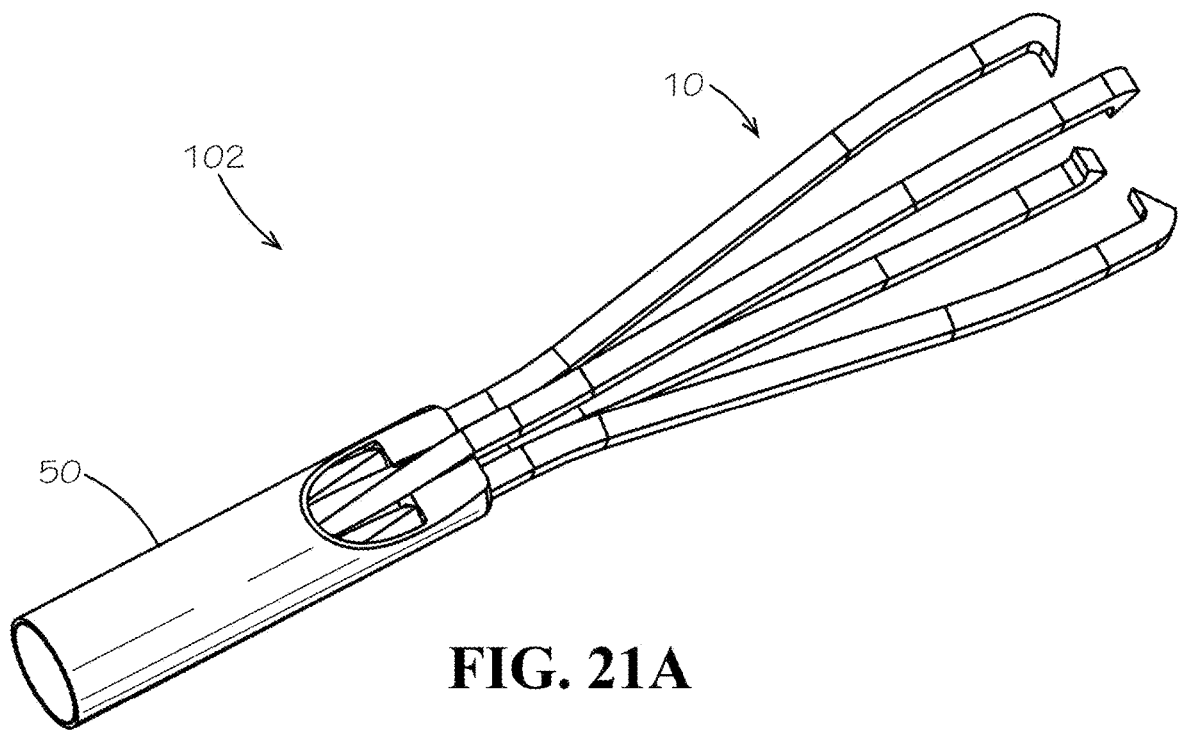
FIG. 21A is a perspective view of an embodiment of an endoscopic clip apparatus in a partially retracted position.
Figure 21B:
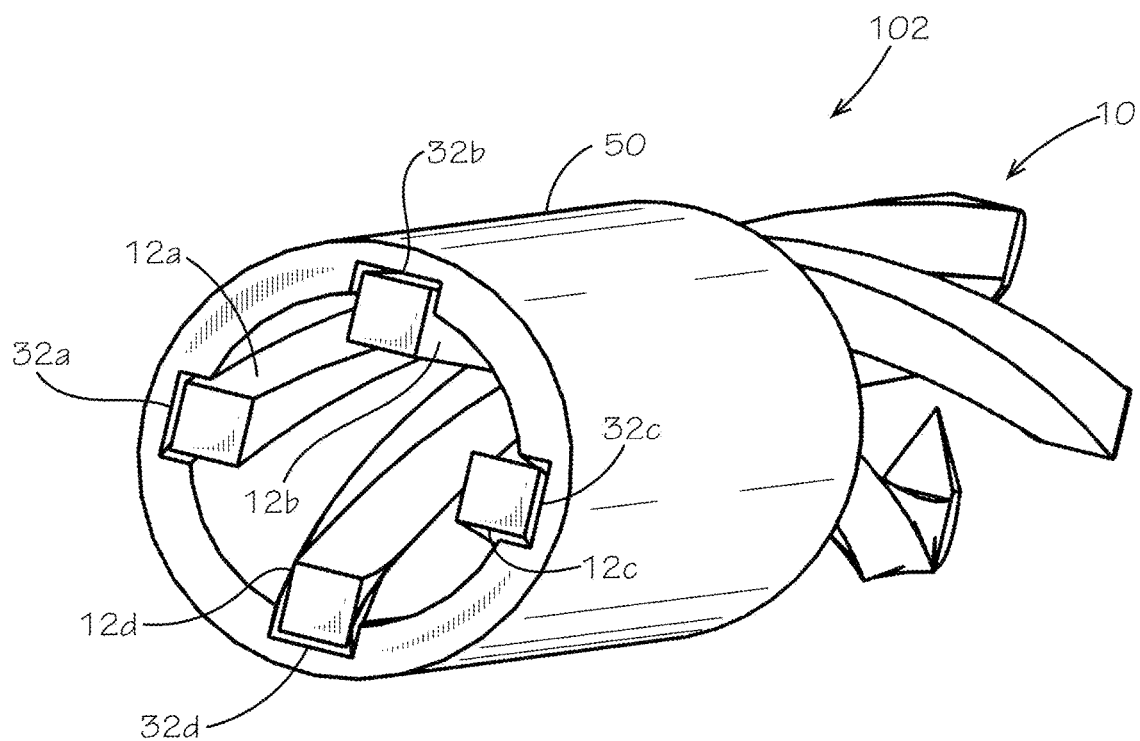
FIG. 21B is a perspective view of an embodiment of an endoscopic clip apparatus in a partially retracted position showing helical channels in the clip sleeve.

Referring to FIG. 20A to FIG. 21B, in some alternative embodiments, clip sleeve 50 includes internal channels 32a, 32b, 32c, 32d formed in a curvilinear orientation on the inner wall of clip sleeve 50 to guide a twisting or cinching motion of clip 10 during retraction. Such a configuration provides a corresponding twisting motion of the arms 12a, 12b, 12c, 12d during retraction as each arm slides in each channel. As shown in FIG. 21A and FIG. 21B, first arm 12a is disposed in first channel 32a, second arm 12b is disposed in second channel 32b, third arm 12c is disposed in third channel 32c, and fourth arm 12d is disposed in fourth channel 32d.

Figure 22:
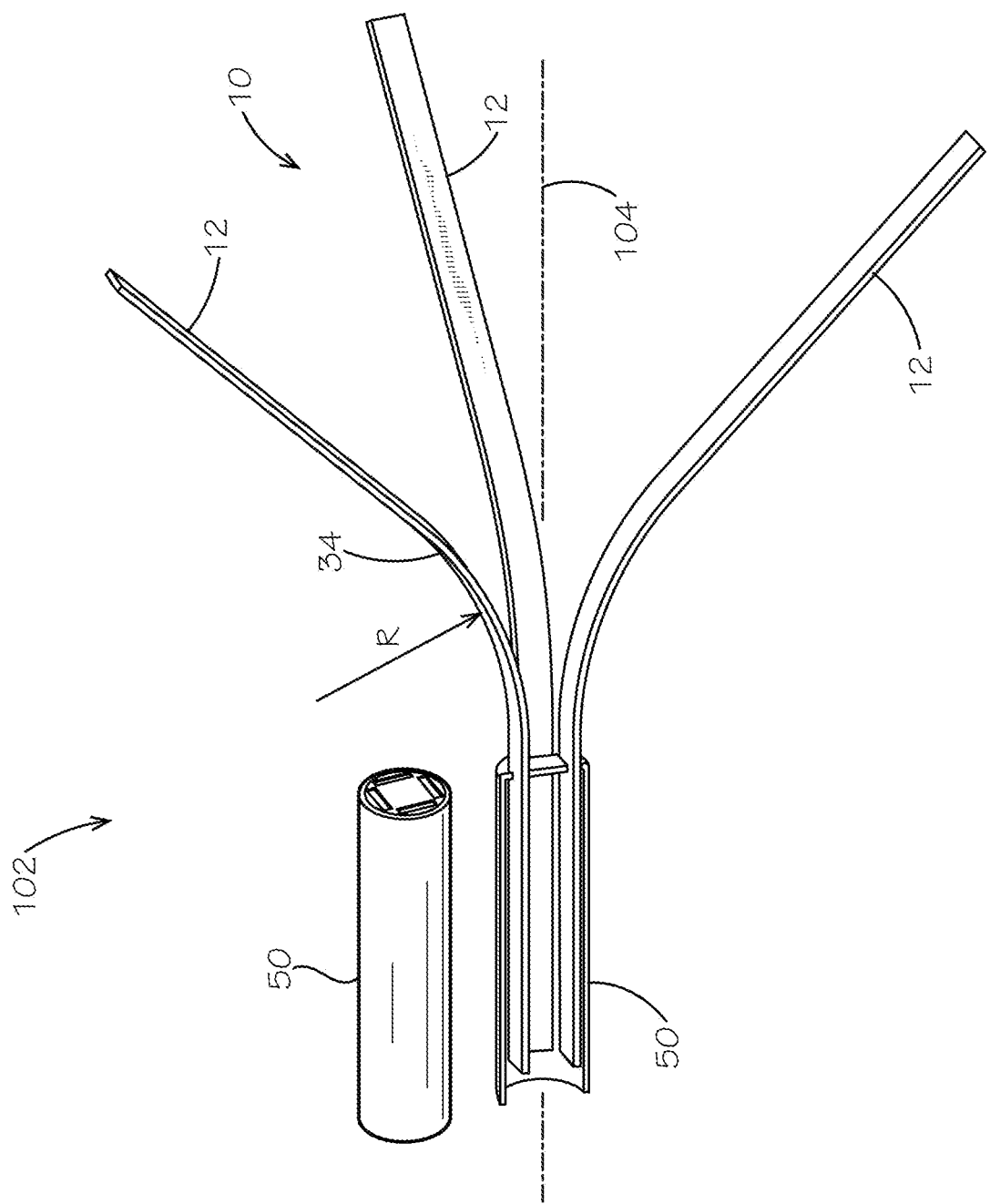
FIG. 22 is a perspective cross-sectional view of an embodiment of an endoscopic clip including arms with convex curved sections curing away from the longitudinal axis.

Referring to FIG. 22, an embodiment of a detachable clip apparatus 102 including a clip 10 with a plurality of arms 12 and a clip sleeve 50, wherein the clip 10 is received in the distal end of the clip sleeve 12. Each arm includes a curved portion 34 including a radius R such that the distal end of each arm curves away from the longitudinal axis 104. As the clip 10 is retracted into clip sleeve 50, the curved portion 34 of each arm is constrained by clip sleeve 50 forcing each distal end of each arm toward longitudinal axis 104. The radius R may be tuned to provide a desired rate of closure. In some embodiments, the location of curved portion 34 can be moved closer to the distal tip of each arm to provide closing later in the retraction stroke. In other embodiments, the location of curved portion 34 can be move away from the distal tip of each arm to provide closing earlier in the retraction stroke.

Figure 23:
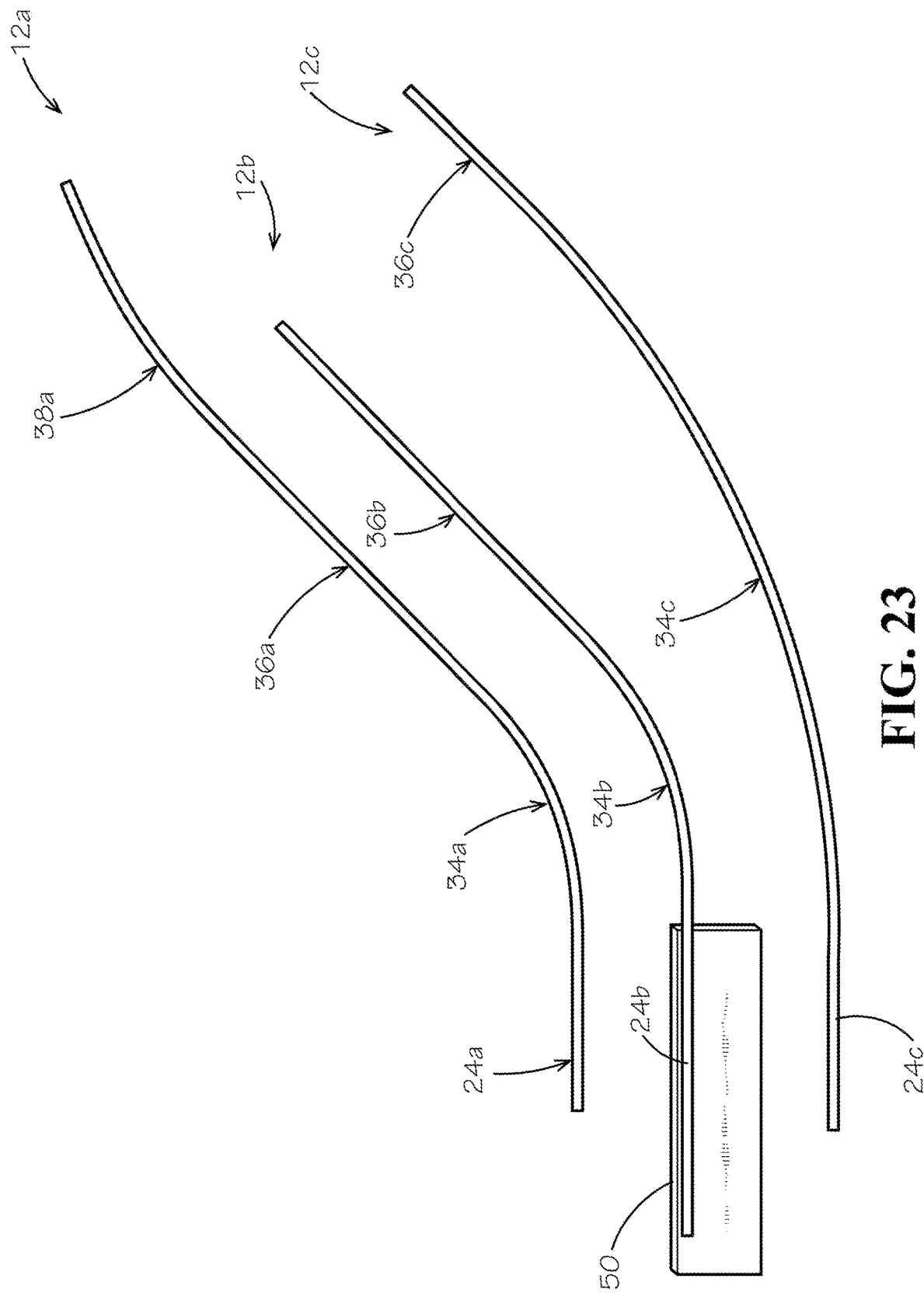
FIG. 23 is a partial cross-sectional side view showing various embodiments of arms for an endoscopic clip including different curvature profiles.

Referring to FIG. 23, various embodiments of arms 12a, 12b, 12c of a clip are shown. First arm 12 includes a first section 24a that is substantially straight and flat, a second curved section 34a with a first convex radius of curvature, a substantially straight and flat third section 36a, and a distal curved fourth section 38a with a second concave radius of curvature at the distal end of the arm. In some embodiments, one or more axially twisted sections may be added to any of the sections along the length of the arm to provide an additional axial twisting motion during axial travel of clamp sleeve 50. The first convex radius of curvature in second curved section 34a causes the arm to close as the arm is constrained by clip sleeve 50 during retraction. The second concave radius of curvature in the fourth curved section 38a at the distal tip of the leg provides controlled clamping force or adjustment of the closing diameter when the clip is nearly fully retracted. An additional embodiment of a leg 12b includes first, second and third sections 24b, 34b and 36b, but does not include a fourth curved section. A further embodiment of a leg 12c includes first, second and third sections 24c, 34c and 36c, having a larger radius along second curved section 34c. By providing a larger radius of curvature in the convex portion along second curved section 34c, the clip will have a slower and more precise opening and closing action as the clip is moved relative to clip sleeve 50.

Referring to FIGS. 24A-26B, additional embodiments of release joint 16 are shown. As shown in FIG. 24A and FIG. 24B, release joint 16 includes a first arm 12a including a first release pin 15a and a second release pin 15b, each projecting radially outwardly from each respective arm. A bushing 43 is disposed at the distal end of the control wire 70, and a loop 42 projects distally from the bushing. A first release tab 44 projects radially inwardly from first arm 12a, and a second release tab 46 projects radially inwardly from second arm 12b opposing first release tab. When release joint is engaged, as shown in FIG. 24A, first and second release tabs 44, 46 fit inside loop 42, thereby securing control wire 70 to clip 10. When first and second release pins 15a, 15b become aligned with corresponding openings in the clip sleeve, the first and second release tabs 44, 46 exit loop 42, thereby releasing the control wire 70 from clip 10. In some embodiments, bushing 42 provides an axial stop for first and second arms 12a, 12b.

Figure 25A:
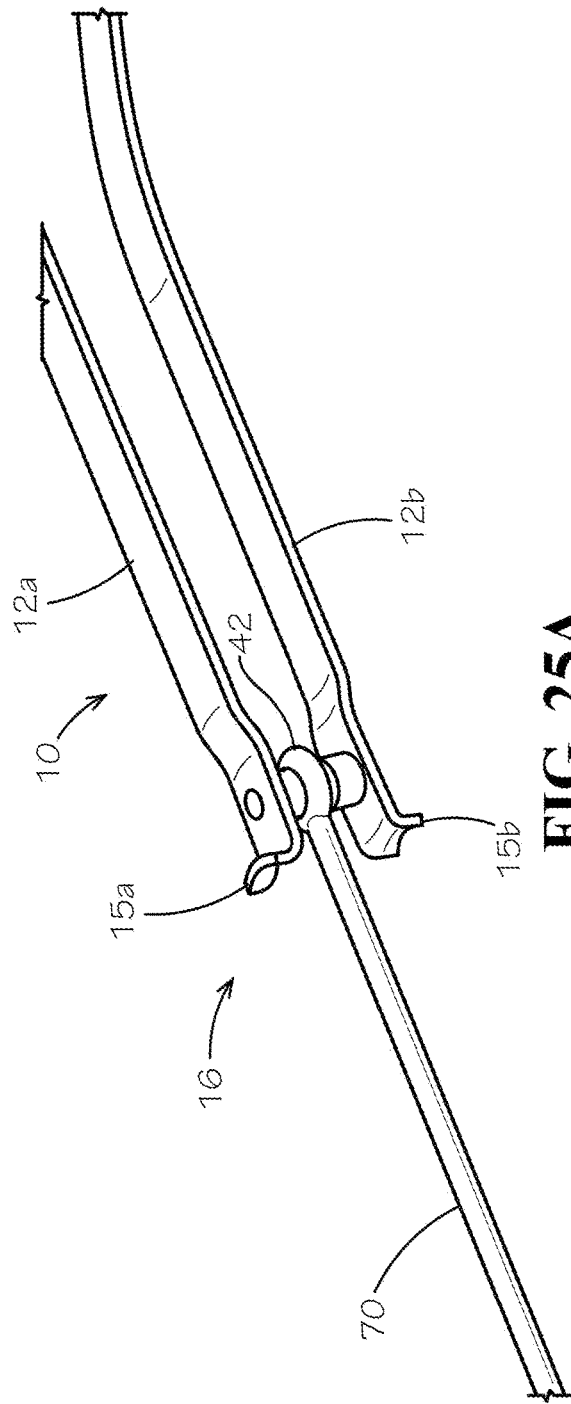
FIG. 25A is a perspective view of an endoscopic clip apparatus including a control wire and a clip with a release joint.
Figure 25B:
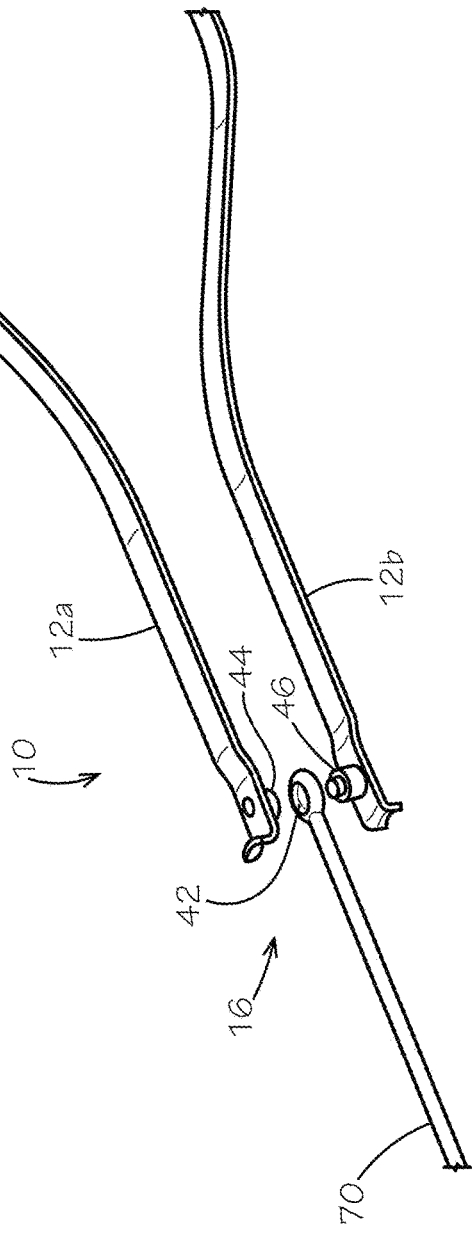
FIG. 25B is a perspective view of an endoscopic clip apparatus including a control wire and a clip with a release joint.

As shown in FIG. 25A and FIG. 25B, an alternative version of release joint 16 includes a control wire with a loop 42 disposed on the distal end of the control wire 70. First and second release tabs 44, 46 project radially inwardly from first and second arms 12a, 12b and reside in loop 42 when control wire 70 is engaged with clip 10. Upon release, first and second release tabs 44, 46 separate from engagement with each other and with loop 42, thereby disengaging control wire 70 from clip 10. In some embodiments, first and second release tabs 44, 46 each include a chamfer, radius or ball extending from each tab to mate with the shape of loop 42.

As shown in FIG. 26A and FIG. 26B, an alternative embodiment of a release joint 16 includes a bushing 43 disposed at the distal end of control wire 70. A post 48 projects distally from bushing 43, having a smaller diameter than bushing 43. A circumferential groove 49 is defined in post 48, and a corresponding protrusion 47 extending radially inwardly from arm 12 is shaped to engage the groove 49. Upon release, projection 47 exits groove 49, thereby disengaging control wire 70 from clip 10. In further embodiments, groove 49 is defined only partially around the circumference of post 48.

Referring further to the disclosure of arms 12 on clip 10, the present disclosure provides arms 12 biased to expand away from the longitudinal axis 104 when extended from clip sleeve 50 during deployment of the clip. The arms are then constrained by clip sleeve 50 during retraction to a closed position. In other embodiments, arms 12 may include a neutrial bias relative to longitudinal axis 104, and are forced away from longitudinal axis 104 to an open configuration upon deployment. The forcing action away from longitudinal axis 104 is provided by the corresponding shape and orientation of the openings at the distal end of the clip sleeve. In further embodiments, the arms are biased toward longitudinal axis 104, and are forced away from longitudinal axis 104 to an open configuration upon deployment by the corresponding shape and orientation of the openings at the distal end of the clip sleeve.

Thus, although there have been described particular embodiments of the present disclosure of a new and useful ENDOSCOPIC CLIP APPARATUS AND METHODS, it is not intended that such references be construed as limitations upon the scope of this disclosure except as set forth in the following claims.

What is claimed is:

1. An apparatus, comprising:
   a clip sleeve defining an interior passage along a longitudinal axis, the clip sleeve having a distal end with a plurality of openings defined in the distal end;
   a clip including a plurality of arms disposed in the clip sleeve, each arm including a distal tip extending from the clip sleeve through one of the plurality of openings, each arm including a convex curved section oriented away from the longitudinal axis; and
   an axially twisted section in at least one of the plurality of arms,
   wherein the clip sleeve and clip are axially moveable relative to each other such that when the clip sleeve travels over the convex curved section of each arm toward the distal tip of each arm, each arm is constrained by the clip sleeve and each distal tip advances toward the longitudinal axis.

2. The apparatus of claim 1, wherein the axially twisted section comprises an axial twist angle between zero and ninety degrees.

3. The apparatus of claim 1, wherein the axially twisted section comprises an axial twist angle between zero and one-hundred-eighty degrees.

4. The apparatus of claim 1, further comprising each of the plurality of arms including a substantially flat section proximal to the convex curved section.

5. The apparatus of claim 4, further comprising a hook disposed on the distal tip of each arm.

6. The apparatus of claim 1, further comprising a release joint disposed on the clip inside the clip sleeve.

7. The apparatus of claim 6, further comprising a control wire disposed inside the clip sleeve, wherein the control wire attaches to the clip at the release joint.

8. The apparatus of claim 7, wherein the release joint comprises a ball and socket.

9. The apparatus of claim 1, wherein the plurality of arms comprises four arms.

10. The apparatus of claim 9, wherein each of the plurality of arms comprises an axially twisted section.

11. An endoscopic clip apparatus, comprising:
    a clip sleeve defining an interior passage along a longitudinal axis, the clip sleeve including distal end defining first, second, third and fourth openings; and
    a clip disposed in the clip sleeve, the clip including a first arm extending through the first opening, a second arm extending through the second opening, a third arm extending through the third opening, and a fourth arm extending through the fourth opening,
    wherein each of the first, second, third and fourth arms includes a section curving away from the longitudinal axis, and
    wherein the clip sleeve and the clip are axially moveable relative to each other along the longitudinal axis.

12. The apparatus of claim 11, further comprising each of the first, second, third and fourth arms including an axially twisted section.

13. The apparatus of claim 12, wherein each axially twisted section includes an axial twist angle less than or equal to ninety degrees.

14. The apparatus of claim 12, wherein each axially twisted section includes an axial twist angle between zero and one-hundred-eighty degrees.

15. The apparatus of claim 11, further comprising each of the first, second, third and fourth arms includes a distal tip.

16. The apparatus of claim 15, further comprising a hook disposed on each distal tip.

17. The apparatus of claim 16, further comprising a flange disposed on each distal tip.

18. A method, comprising:
   providing an endoscopic clip apparatus including a clip sleeve defining an interior passage along a longitudinal axis, the clip sleeve including distal end defining first, second, third and fourth openings, and including a clip disposed in the clip sleeve, the clip including a first arm extending through the first opening, a second arm extending through the second opening, a third arm extending through the third opening, and a fourth arm extending through the fourth opening, wherein each of the first, second, third and fourth arms includes a section curving away from the longitudinal axis;
   translating the clip relative to the clip sleeve;
   constraining the arms in the clip sleeve such that the arms move toward the longitudinal axis.

19. The method of claim 18, further comprising rotating the arms relative to the clip sleeve.

20. An apparatus, comprising:
   a clip sleeve defining an interior passage along a longitudinal axis, the clip sleeve having a distal end with a plurality of openings defined in the distal end; and
   a clip including a plurality of arms disposed in the clip sleeve, each arm including a distal tip extending from the clip sleeve through one of the plurality of openings, each arm including a convex curved section oriented away from the longitudinal axis,
   wherein the plurality of arms comprises four arms, and
   wherein the clip sleeve and clip are axially moveable relative to each other such that when the clip sleeve travels over the convex curved section of each arm toward the distal tip of each arm, each arm is constrained by the clip sleeve and each distal tip advances toward the longitudinal axis.

21. The apparatus of claim 20, further comprising an axially twisted section in at least one of the plurality of arms.

22. The apparatus of claim 21, wherein the axially twisted section comprises an axial twist angle between zero and ninety degrees.

23. The apparatus of claim 21, wherein the axially twisted section comprises an axial twist angle between zero and one-hundred-eighty degrees.

24. The apparatus of claim 20, further comprising each of the plurality of arms including a substantially flat section proximal to the convex curved section.

25. The apparatus of claim 24, further comprising a hook disposed on the distal tip of each arm.

26. The apparatus of claim 20, further comprising a release joint disposed on the clip inside the clip sleeve.

27. The apparatus of claim 26, further comprising a control wire disposed inside the clip sleeve, wherein the control wire attaches to the clip at the release joint.

28. The apparatus of claim 27, wherein the release joint comprises a ball and socket.

29. The apparatus of claim 20, wherein each of the plurality of arms comprises an axially twisted section.

* * * * *